US011446064B2

(12) United States Patent
Sharifi-Mehr et al.

(10) Patent No.: US 11,446,064 B2
(45) Date of Patent: Sep. 20, 2022

(54) ORTHOPEDIC GROWING DEVICES

(71) Applicant: Stryker European Operations Holdings LLC, Kalamazoo, MI (US)

(72) Inventors: Amir Ali Sharifi-Mehr, Bloomingdale, NJ (US); Oliver Buchert, Franklin Lakes, NJ (US); Andrew Poutiatine, Mill Valley, CA (US); Philip Harris Frank, Maplewood, NJ (US); Charles L. Bush, Jr., Wayne, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 165 days.

(21) Appl. No.: 16/394,303

(22) Filed: Apr. 25, 2019

(65) Prior Publication Data
US 2019/0328425 A1 Oct. 31, 2019

Related U.S. Application Data

(60) Provisional application No. 62/662,993, filed on Apr. 26, 2018.

(51) Int. Cl.
*A61B 17/70* (2006.01)
*A61B 17/72* (2006.01)
(Continued)

(52) U.S. Cl.
CPC ...... *A61B 17/7017* (2013.01); *A61B 17/7025* (2013.01); *A61B 17/7216* (2013.01);
(Continued)

(58) Field of Classification Search
CPC ............. A61B 17/7017; A61K 9/0004; A61M 5/14526
See application file for complete search history.

(56) References Cited

U.S. PATENT DOCUMENTS

| 3,976,060 A | 8/1976 | Hildebrandt et al. |
| 4,078,559 A | 3/1978 | Nissinen |

(Continued)

FOREIGN PATENT DOCUMENTS

| EP | 3047810 A1 | 7/2016 |
| JP | H9504185 A | 4/1997 |

(Continued)

OTHER PUBLICATIONS

Australian Search Report for Application No. AU2017216532 dated Sep. 10, 2019, 1 page.
(Continued)

*Primary Examiner* — Jan Christopher L Merene
(74) *Attorney, Agent, or Firm* — Lerner, David, Littenberg, Krumholz & Mentlik, LLP

(57) ABSTRACT

An expandable rod system includes a first rod portion having an internal cavity, a second rod portion sealingly positioned within the internal cavity of the first rod portion and moveable in a first axial direction relative to the first rod portion, and an osmotic chamber for receiving an osmotic agent to facilitate movement of the second rod portion to expand the rod system. The rod system includes a lock assembly engageable with the second rod portion to prevent the second rod portion from moving in a second axial direction. The lock assembly includes a tapered ramped portion and a bearing member that is moveable within the tapered ramped portion such that when compression forces are imparted on the second rod portion, the bearing member becomes wedged in the tapered ramped portion.

19 Claims, 15 Drawing Sheets

(51) Int. Cl.
*A61B 17/80* (2006.01)
*A61B 17/00* (2006.01)
*A61B 17/68* (2006.01)

(52) U.S. Cl.
CPC ..... *A61B 17/8023* (2013.01); *A61B 2017/00539* (2013.01); *A61B 2017/681* (2013.01)

(56) References Cited

U.S. PATENT DOCUMENTS

| | | | |
|---|---|---|---|
| 4,157,715 A * | 6/1979 | Westerhoff | A61B 17/8004 606/60 |
| 4,289,123 A | 9/1981 | Dunn | |
| 4,445,513 A | 5/1984 | Ulrich et al. | |
| 4,611,580 A | 9/1986 | Wu | |
| 4,611,582 A | 9/1986 | Duff | |
| 4,658,809 A | 4/1987 | Ulrich et al. | |
| 4,827,918 A | 5/1989 | Olerud | |
| 4,931,055 A | 6/1990 | Bumpus et al. | |
| 4,957,495 A | 9/1990 | Kluger | |
| 4,969,884 A * | 11/1990 | Yum | A61K 9/0004 604/218 |
| 5,034,011 A | 7/1991 | Howland | |
| 5,129,388 A | 7/1992 | Vignaud et al. | |
| 5,330,472 A | 7/1994 | Metz-Stavenhagen | |
| 5,350,379 A | 9/1994 | Spievack | |
| 5,505,733 A | 4/1996 | Justin et al. | |
| 5,575,790 A | 11/1996 | Chen et al. | |
| 5,626,579 A | 5/1997 | Muschler et al. | |
| 5,704,939 A | 1/1998 | Justin | |
| 5,720,746 A | 2/1998 | Soubeiran | |
| 5,762,599 A | 6/1998 | Sohn | |
| 5,810,815 A | 9/1998 | Morales | |
| 6,245,075 B1 | 6/2001 | Betz et al. | |
| 6,416,516 B1 | 7/2002 | Stauch et al. | |
| 6,417,750 B1 | 7/2002 | Sohn | |
| 6,500,177 B1 | 12/2002 | Martinelli et al. | |
| 6,783,530 B1 | 8/2004 | Levy | |
| 6,849,076 B2 | 2/2005 | Blunn et al. | |
| 6,918,910 B2 | 7/2005 | Smith et al. | |
| 7,011,658 B2 | 3/2006 | Young | |
| 7,063,706 B2 | 6/2006 | Wittenstein | |
| 7,135,022 B2 | 11/2006 | Kosashvili et al. | |
| 7,481,841 B2 | 1/2009 | Hazebrouck et al. | |
| 7,655,026 B2 | 2/2010 | Justis et al. | |
| 7,666,184 B2 | 2/2010 | Stauch | |
| 7,666,207 B2 | 2/2010 | Schlapfer et al. | |
| 7,699,879 B2 | 4/2010 | Sherman et al. | |
| 7,753,915 B1 | 7/2010 | Eksler et al. | |
| 7,763,053 B2 | 7/2010 | Gordon | |
| 7,776,075 B2 | 8/2010 | Bruneau et al. | |
| 7,776,091 B2 | 8/2010 | Mastrorio et al. | |
| 7,780,705 B2 | 8/2010 | Shaolian et al. | |
| 7,806,913 B2 | 10/2010 | Fanger et al. | |
| 7,842,036 B2 | 11/2010 | Phillips | |
| 7,927,357 B2 | 4/2011 | Sacher et al. | |
| 7,938,848 B2 | 5/2011 | Sweeney | |
| 7,942,908 B2 | 5/2011 | Sacher et al. | |
| 7,955,357 B2 | 6/2011 | Kiester | |
| 8,016,837 B2 | 9/2011 | Giger et al. | |
| 8,016,860 B2 | 9/2011 | Carl et al. | |
| 8,043,290 B2 | 10/2011 | Harrison et al. | |
| 8,057,472 B2 | 11/2011 | Walker et al. | |
| 8,092,499 B1 | 1/2012 | Roth | |
| 8,100,943 B2 | 1/2012 | Malandain et al. | |
| 8,114,133 B2 | 2/2012 | Logan | |
| 8,142,454 B2 | 3/2012 | Harrison et al. | |
| 8,177,812 B2 | 5/2012 | Sankaran | |
| 8,202,301 B2 | 6/2012 | Prevost et al. | |
| 8,211,149 B2 | 7/2012 | Justis | |
| 8,252,063 B2 | 8/2012 | Stauch | |
| 8,277,489 B2 | 10/2012 | Saidha et al. | |
| 8,287,541 B2 | 10/2012 | Nelson et al. | |
| 8,292,927 B2 | 10/2012 | Rouleau et al. | |
| 8,298,240 B2 | 10/2012 | Giger et al. | |
| 8,343,192 B2 | 1/2013 | Kiester | |
| 8,372,121 B2 | 2/2013 | Capote et al. | |
| 8,439,915 B2 | 5/2013 | Harrison et al. | |
| 8,475,499 B2 | 7/2013 | Cournoyer et al. | |
| 8,486,112 B2 | 7/2013 | Fanger et al. | |
| 8,568,457 B2 | 10/2013 | Hunziker | |
| 8,585,740 B1 | 11/2013 | Ross et al. | |
| 8,623,036 B2 | 1/2014 | Harrison et al. | |
| 8,663,285 B2 | 3/2014 | Dall et al. | |
| 8,721,643 B2 | 5/2014 | Morgan et al. | |
| 8,764,751 B2 | 7/2014 | Orbay et al. | |
| 8,777,947 B2 | 7/2014 | Zahrly et al. | |
| 8,814,909 B2 | 8/2014 | Fanger et al. | |
| 8,852,233 B2 | 10/2014 | Burke | |
| 8,894,663 B2 | 11/2014 | Giger et al. | |
| 8,894,688 B2 | 11/2014 | Suh | |
| 8,915,915 B2 | 12/2014 | Harrison et al. | |
| 8,915,917 B2 | 12/2014 | Doherty et al. | |
| 8,956,392 B2 | 2/2015 | Khatchadourian et al. | |
| 8,961,567 B2 | 2/2015 | Hunziker | |
| 8,974,500 B2 | 3/2015 | Khatchadourian et al. | |
| 8,992,527 B2 | 3/2015 | Guichet | |
| 9,060,810 B2 | 6/2015 | Kercher et al. | |
| 9,144,438 B2 | 9/2015 | Suh | |
| 9,919,082 B2 * | 3/2018 | Harder | A61M 1/84 |
| 2002/0173757 A1 * | 11/2002 | Swisher | A61M 1/61 604/317 |
| 2003/0144669 A1 * | 7/2003 | Robinson | A61B 17/66 606/90 |
| 2003/0220643 A1 | 11/2003 | Ferree | |
| 2004/0023623 A1 | 2/2004 | Stauch et al. | |
| 2005/0229934 A1 * | 10/2005 | Willeford | A61M 16/209 128/200.26 |
| 2005/0277921 A1 | 12/2005 | Eisermann et al. | |
| 2006/0106381 A1 | 5/2006 | Ferree et al. | |
| 2006/0293683 A1 | 12/2006 | Stauch | |
| 2007/0010814 A1 | 1/2007 | Stauch | |
| 2007/0027230 A1 * | 2/2007 | Beyar | A61L 24/043 523/117 |
| 2007/0050036 A1 | 3/2007 | Felt et al. | |
| 2007/0255237 A1 | 11/2007 | Lobl et al. | |
| 2008/0027436 A1 | 1/2008 | Cournoyer et al. | |
| 2008/0045951 A1 | 2/2008 | Fanger et al. | |
| 2008/0177319 A1 | 7/2008 | Schwab | |
| 2008/0208260 A1 | 8/2008 | Truckai et al. | |
| 2009/0030462 A1 | 1/2009 | Buttermann | |
| 2009/0112207 A1 | 4/2009 | Walker et al. | |
| 2009/0118774 A1 | 5/2009 | Miller, III | |
| 2009/0127288 A1 * | 5/2009 | Keller | B05C 17/00579 222/1 |
| 2009/0204156 A1 | 8/2009 | McClintock et al. | |
| 2009/0234388 A1 | 9/2009 | Patterson et al. | |
| 2009/0275984 A1 | 11/2009 | Kim et al. | |
| 2009/0306717 A1 | 12/2009 | Kercher et al. | |
| 2010/0106192 A1 | 4/2010 | Barry | |
| 2010/0137913 A1 | 6/2010 | Khatchadourian et al. | |
| 2010/0137914 A1 | 6/2010 | Ritland | |
| 2010/0152776 A1 | 6/2010 | Keyer et al. | |
| 2010/0211105 A1 | 8/2010 | Moumene et al. | |
| 2010/0318130 A1 | 12/2010 | Parlato et al. | |
| 2011/0097377 A1 * | 4/2011 | Serhan | A61K 31/65 606/301 |
| 2011/0184463 A1 | 7/2011 | Schwend | |
| 2011/0196371 A1 | 8/2011 | Forsell | |
| 2011/0196435 A1 | 8/2011 | Forsell | |
| 2011/0238126 A1 | 9/2011 | Soubeiran | |
| 2012/0035661 A1 | 2/2012 | Pool et al. | |
| 2012/0053633 A1 | 3/2012 | Stauch | |
| 2012/0130428 A1 | 5/2012 | Hunziker | |
| 2012/0130432 A1 | 5/2012 | Ferree et al. | |
| 2012/0271353 A1 | 10/2012 | Barry | |
| 2012/0296234 A1 | 11/2012 | Wilhelm et al. | |
| 2013/0072932 A1 | 3/2013 | Stauch | |
| 2013/0096615 A1 | 4/2013 | Kiester | |
| 2013/0150889 A1 | 6/2013 | Fening et al. | |
| 2013/0206137 A1 * | 8/2013 | Greter | B05C 17/00593 128/200.21 |
| 2013/0282064 A1 | 10/2013 | Arnin | |
| 2013/0338713 A1 | 12/2013 | Kawakami et al. | |

(56) References Cited

U.S. PATENT DOCUMENTS

| | | |
|---|---|---|
| 2013/0338714 A1 | 12/2013 | Chang et al. |
| 2014/0074168 A1 | 3/2014 | Mundis et al. |
| 2014/0135769 A1 | 5/2014 | Ziran |
| 2014/0142631 A1 | 5/2014 | Hunziker |
| 2014/0222074 A1 | 8/2014 | Rathbun et al. |
| 2014/0277147 A1 | 9/2014 | Alexander et al. |
| 2014/0296918 A1 | 10/2014 | Fening et al. |
| 2014/0324047 A1 | 10/2014 | Zahrly et al. |
| 2015/0051647 A1 | 2/2015 | Suh |
| 2015/0127002 A1 | 5/2015 | Doherty et al. |
| 2015/0134002 A1 | 5/2015 | Khatchadourian et al. |
| 2015/0150601 A1 | 6/2015 | Giger et al. |
| 2015/0157364 A1 | 6/2015 | Hunziker |
| 2016/0120580 A1 | 5/2016 | Johnston, Jr. et al. |
| 2016/0199101 A1* | 7/2016 | Sharifi-Mehr ..... A61B 17/7004 606/258 |
| 2017/0095273 A1 | 4/2017 | Lynch et al. |
| 2017/0151422 A1* | 6/2017 | Argentine ............. A61M 5/178 |
| 2018/0028234 A1 | 2/2018 | Simpson et al. |
| 2018/0110504 A1* | 4/2018 | McAfee ................ A61F 2/4455 |

FOREIGN PATENT DOCUMENTS

| | | |
|---|---|---|
| JP | 2009535155 A | 10/2009 |
| JP | 2011502003 A | 1/2011 |
| JP | 2011072471 A | 4/2011 |
| WO | 9009156 A1 | 8/1990 |
| WO | 9522292 A1 | 8/1995 |
| WO | 2007090021 A1 | 8/2007 |
| WO | 2007123920 A2 | 11/2007 |
| WO | 2010062718 A1 | 6/2010 |
| WO | 2011027126 A1 | 3/2011 |
| WO | 2011068851 A1 | 6/2011 |
| WO | 2011116773 A1 | 9/2011 |
| WO | 2012024335 A2 | 2/2012 |
| WO | 2012044371 A1 | 4/2012 |

OTHER PUBLICATIONS

Extended European Search Report for Application No. EP19171279.3 dated Sep. 3, 2019, pp. 1-4.

* cited by examiner

ORTHOPEDIC GROWING DEVICES

CROSS-REFERENCE TO RELATED APPLICATIONS

The present application claims the benefit of the filing date of U.S. Provisional Patent Application No. 62/662,993 filed Apr. 26, 2018, the disclosure of which is hereby incorporated herein by reference.

BACKGROUND OF THE INVENTION

The present disclosure relates to orthopedic devices capable of expansion for use in treating a variety of bone deformities.

There are many instances in treating orthopedic conditions that having a device that can vary its size could be beneficial. For instance, in pediatric patients, devices are often implanted to correct the orthopedic condition and remain implanted for a period of time to maintain the corrected position. However, as the patient grows, it is desirable for the implanted device to grow with the patient to allow proper development of the bones. This is particularly true in the case of correction of spinal disorders, such as scoliosis, that result in spinal columns exhibiting abnormal curvatures. These maladies may result in pain and partial or complete loss of mobility. To correct the abnormal curvature, surgeons have implanted spinal rods on patient's spinal columns. These rods exert a force on the spinal column to correct and restore the natural curvature thereof. However, when the patient is young, such as in pediatric scoliosis, the spinal column is still growing, and fixed-length rods prevent further thoracic growth in the patient. As a result, expandable spinal rods have been developed to accommodate the growing spine of pediatric patients.

Existing expandable rods typically rely upon intricate actuation means, such as the use of magnets and motors to cause distraction of separate rod portions to lengthen the overall rod. However, during surgery, the rod is not susceptible to common medical imaging techniques, such as the commonly used magnetic resonance imaging (MRI). Alternatively, expandable rods may be mechanically distractible rods that employ manually movable rods with the use of a distraction instrument. However, these rods require numerous subsequent invasive surgical interventions to lengthen the rod as the patient grows.

Thus, improvements for expandable devices that can be used for predictable distraction over time are needed.

BRIEF SUMMARY OF THE INVENTION

A first aspect of the disclosure includes an expandable rod system including a first portion having an internal cavity, a second rod portion positioned within the internal cavity of the first rod portion and moveable in a first axial direction relative to the first rod portion, and an osmotic chamber for receiving an osmotic agent to facilitate movement of the second rod portion to expand the rod system.

In other embodiments, the rod system may include a semi-permeable membrane fluidly connected to the osmotic chamber for allowing fluid from the patient to flow across the membrane and into the osmotic chamber. The second rod portion may be sealingly positioned within the internal cavity of the first rod portion. The rod system may include a lock assembly engageable with the second rod portion to prevent the second rod portion from moving in a second axial direction. The lock assembly may include a tapered ramped portion and a bearing member, the bearing member may be moveable within the tapered ramped portion. When compression forces are imparted on the second rod portion, the bearing member may become wedged in the tapered ramped portion. The rod system may include an access hole to permit access of an instrument through the access hole such that when the bearing member is wedged in the tapered ramped portion, the instrument may dislodge the bearing member from the tapered ramped portion. The instrument may be configured to dislodge the bearing member and push the bearing member up the ramped portion to allow movement of the second rod portion relative to the first rod portion in the second direction. The instrument may have a forked end shape. The bearing member may be a ball. The second rod portion and the internal cavity may be curved. The rod system may include a pressure relief system. The pressure relief system may include a spring-loaded ball. The osmotic chamber may be positioned within a portion of the internal cavity. The rod system may include a pump configured for implantation sub-dermally in a patient, and the pump may include the osmotic chamber and may be fluidly connected with the internal cavity of the first rod portion. The pump may include a hydraulic fluid chamber for receiving hydraulic fluid. The pump may include a one-way pressure valve to prevent pressure from traveling from the internal cavity to the pump. The second rod portion may be continuously moveable relative to the first rod portion. The second rod portion may be moveable at a constant rate. The rod system may be configured for implantation on a patient's mandible, spinal column, or cranium. The first rod portion may be adapted for connection with a first bone, and the second rod portion may be adapted for connection with a second bone.

A second aspect of the disclosure includes an expandable rod system including a first rod portion including an internal cavity, a second rod portion sealingly positioned within the internal cavity of the first rod portion and moveable in a first axial direction relative to the first rod portion, an osmotic chamber for receiving an osmotic agent to facilitate movement of the second rod portion to expand the rod system, and a semi-permeable membrane fluidly connected to the osmotic chamber for allowing water to flow across the semi-permeable membrane and into the osmotic chamber.

In other embodiments, the rod system may include a sleeve disposed within the internal cavity and extending along a portion of the length of the internal cavity. The sleeve may form a seal between the second rod portion and the first rod portion.

A third aspect of the disclosure includes a method of operating an expandable rod system including engaging a first rod portion with a first a first fixation element implanted in a bone, the first rod portion including a hydraulic cylinder including an internal cavity; engaging a second rod portion with a second fixation element implanted in a second bone, the second rod portion being inserted within the internal cavity of the hydraulic cylinder and sealingly engaging the hydraulic cylinder to thereby define a hydraulic pressure chamber; and inserting an osmotic agent within an osmotic chamber of a pumping system, the osmotic agent having a different concentration of solute from the solute of the patient's fluid, such that the patient's fluid enters into the osmotic chamber creating the pressure that exerts a force on the second rod portion causing it to move in an expansion direction.

In other embodiments, the method may include implanting an osmotic pump having the osmotic chamber sub-dermally in the patient. The method may include injecting hydraulic fluid into an injection port to initially distract the second rod portion.

DETAILED DESCRIPTION

Referring to FIGS. 1-4, a hydraulically expandable spinal rod system 10 according to one embodiment of the present disclosure is shown. The rod, as shown, is designed to be implanted in a spinal column with opposing ends 22, 42 having a fixation member to secure the rod system to respective bone elements or vertebrae of the spinal column via a pedicle screw or the like. For instance, pedicle screws may include a head with an open channel or tulip for accommodating a portion of the rod and a threaded screw shank for insertion into the spinal column. Rather than pedicle screws, spinal hooks or other common fixation devices may be employed. The rod system utilizes hydraulic technology to achieve expansion, as described in greater detail below. Thus, rod system 10 allows for initial distraction of the vertebrae as well as continued expansion after the initial implantation to accommodate changing surgical parameters, including the growth of the patient.

Figure 1:
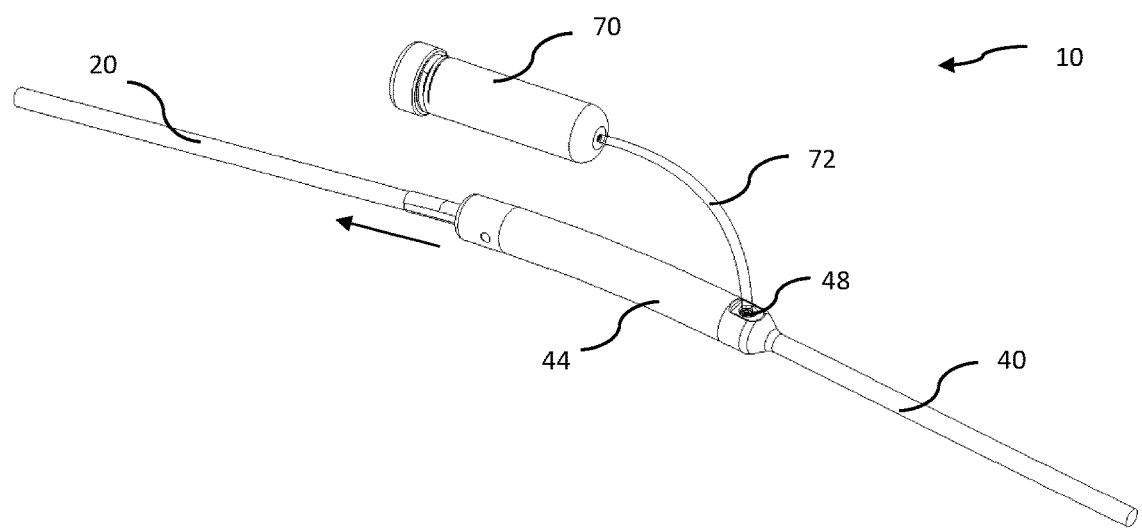
FIG. 1 is a perspective view of an expandable hydraulic rod system according to one embodiment of the present disclosure.
Figure 2:
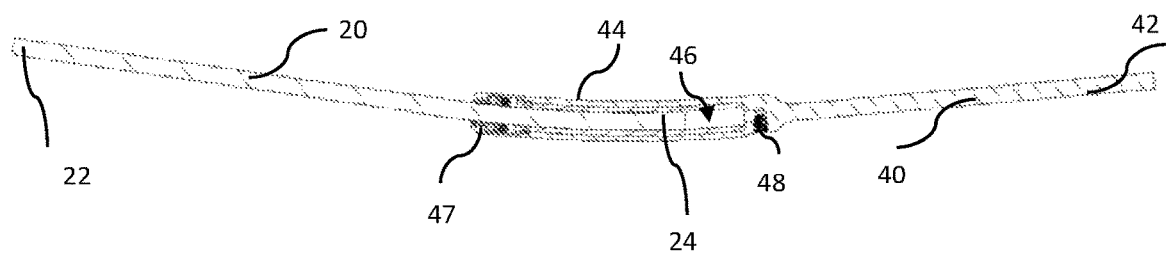
FIG. 2 is a cross-sectional view of the hydraulic rod of FIG. 1.

As shown in FIGS. 1-3, spinal rod system 10 includes multiple rod portions forming a spinal rod, in particular a piston rod 20 and a static rod 40. In the illustrated embodiment, both static rod 40 and piston rod 20 exhibit a predetermined lordotic curve, with a radius of curvature intended to substantially match the physiological curvature of the spine. For example, the radius of curvature of rod system 10 may be in a range between about 100-800 millimeters (mm). This radius of curvature allows the rod system 10 to contour to the spinal sagittal curvature. Alternatively, the rods may be curved to accommodate a spinal column exhibiting a kyphotic curvature such that the piston rod may be designed for fixation to the thoracic spine. Of course, static rod 40 and piston rod 20 may be designed to be bent in any direction or any combination suitable for the needs of the patient, including during a surgical procedure by a surgeon.

Static and piston rods 40, 20 may be formed of any materials suitable for implantation within a patient's body, and preferably are constructed of a metal such as stainless steel alloys, titanium and its alloys, cobalt-chromium-molybdenum alloy (CoCrMo), etc.

Figure 3A:
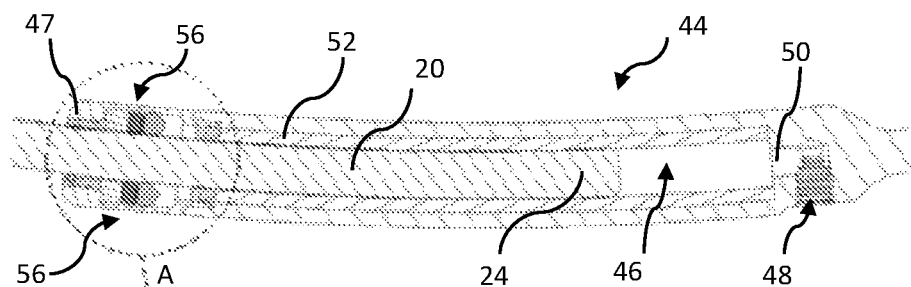
FIG. 3A is an enlarged cross-sectional view of the hydraulic rod portion of the system of FIG. 1, focusing on a lock mechanism.
Figure 3B:
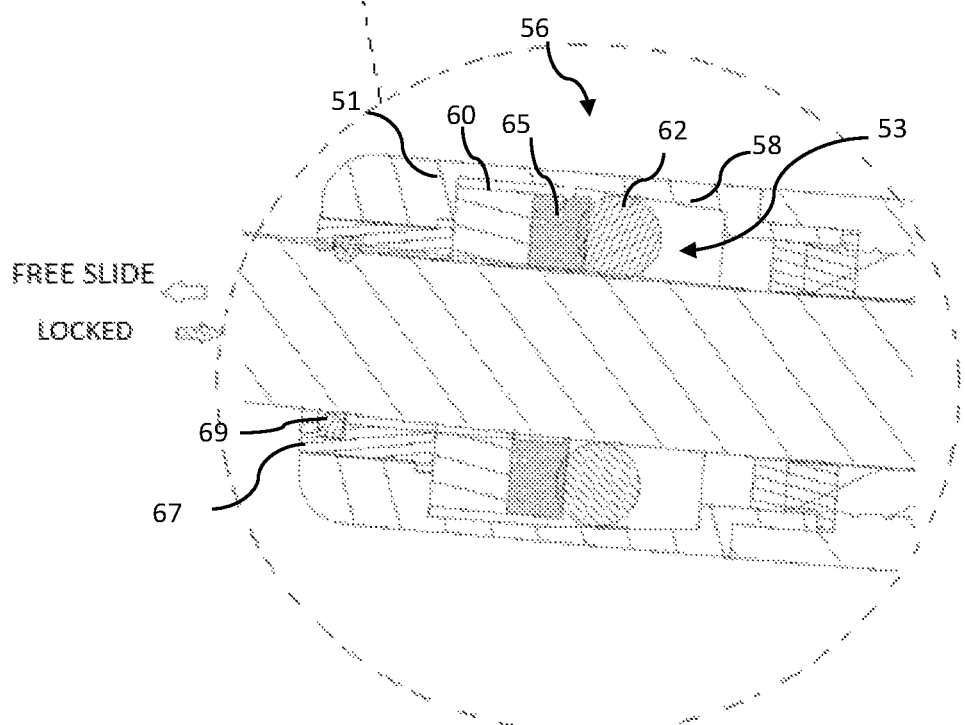
FIG. 3B is a further enlarged cross-sectional view further focusing on the area of the hydraulic rod denoted by circle A of FIG. 3A.

FIGS. 2-3 depict cross-sectional views of the spinal rod system 10, with greater detail of the components of the rods being shown in FIGS. 3A and 3B. As shown in FIG. 2, piston rod 20 is an elongate rod with opposing ends 22, 24. First end 22 is adapted to cooperate with an attachment feature, such as a pedicle screw, for attaching the rod to a first vertebra. In the illustrated embodiment, piston rod 20 has a circular profile, although in other examples it may have an irregular, non-circular shape, which may prevent the piston rod from rotating in the assembled configuration. For example, the piston rod may be keyed or may have a flat section running along a portion or all of the length.

Static rod 40 includes an elongate rod section and a hydraulic cylinder 44. In the illustrated embodiment, static rod 40 is integral or monolithic with the hydraulic cylinder, such that it is constructed as a single piece. In other examples, the static rod and hydraulic rod may be manufactured as two separate pieces fixed together, such as by welding or any other known method. End 42 of static rod 40 may include an attachment feature, like the attachment feature of first end 22 of piston rod 20, so that end 42 of the static can be secured to a second vertebra of the spinal column. Hydraulic cylinder extends to end 47, opposite the elongate section of the static rod and has a substantially curved shape.

Hydraulic cylinder 44 includes internal cavity 46 that is cylindrical in shape and is sized and shaped to receive at least end portion 24 of the piston rod 20. Hydraulic cylinder 44 includes an access port 48 for access of hydraulic fluid into the internal cavity 46. In the illustrated embodiment, the access port 48 is threaded to receive and secure a coupling tube 72 to the access port as shown in FIG. 1. Access port 48 leads into hydraulic pressure chamber 50. In the illustrated embodiment, chamber 50 is cylindrical and is sealed at one end by the elongate section of static rod 40 and fluidly communicates with internal cavity 46 at the other end of the chamber. Chamber 50 may form a portion of the internal cavity 46. Internal cavity 46 includes sleeve 52 shaped as a tube with two opposing open ends that is positioned within the internal cavity. Sleeve 52 extends along at least a portion of the internal cavity and may extend along the entire length of the internal cavity. Sleeve 52 acts as a fluid seal of the hydraulic cylinder 44 by maintaining a seal with the piston rod 20, including along the curvature of the hydraulic cylinder 44. Sleeve 52 may be formed of silicone, ethylene propylene diene monomer rubber ("EPMD" rubber), nylon, or other thermoplastics.

As shown in the illustrated embodiment, hydraulic cylinder 44 receives a portion of piston rod 20. The piston rod is positioned within internal cavity 46 and with sleeve 52 surrounding the piston rod. Piston rod 20 is axially moveable within the internal cavity. Piston rod 20 translates within the internal cavity in the direction shown by the arrow in FIG. 1, such that second end 24 moves away from end 42 of the static rod 40. In this manner, rod system 10 expands to different lengths. As piston rod 20 moves in the expansion direction, end 24 of the piston rod contacts a new portion of the sleeve 52 and forms a seal with it. As a result, the sleeve provides a fresh sealing surface as the piston rod system expands, which improves the ability of the system to maintain a seal after expansion.

Rod system 20 includes a one-way locking mechanism that allows the piston rod 20 to move in an expansion direction but prevents the piston rod from moving in the opposite direction, which prevents undesired collapse of the rod.

Referring to FIGS. 3A and 3B, hydraulic cylinder 44 includes a lock body 51 connected to hydraulic cylinder 44 near end 47 of the hydraulic cylinder opposite the hydraulic pressure chamber 50. Lock body 51 may be constructed as a monolithic piece with the hydraulic cylinder or they may be two separate pieces securedly fixed together. Lock body 51 includes lock assembly 56 which allows for one-direction locking of the piston rod 20 with respect to the static rod 40. In particular, assembly 56 is defined by a cavity 53 of lock body 51, which has a ramped portion 58. Ramped portion 58 extends along a declined plane, such that the ramp declines in the contraction direction, opposite the expansion direction. In other words, the ramp declines in a direction from end 47 of internal cavity 46 to the elongate section of the static rod 40. Lock assembly 56 includes at least one bearing member or ball bearing 62, and in the illustrated embodiment, two ball bearings 62 that are each positioned within a cavity 53 on opposing sides of the lock body. Ball bearings 62 are moveable within the cavity such that the bearings can move down the ramped portion. Lock body 51 further includes a low friction bushing 65 positioned adjacent the ball bearing 62, and an elastomer spring 60 adjacent the bushing for reducing the friction and wear of the piston rod while allowing for expansion of the rod. As such, lock assembly 56 allows for axially expansion of the rod with minimal drag. In the event piston rod 20 is subjected to compression, ball bearings 62 move in the contraction direction and become wedged into the tapered ramped portion 58. With the ball bearings 62 wedged into the ramped portion 58, the ball bearings exert a force or bear on the piston rod to lock the piston rod in place.

Lock body 51 also includes bushing 67 at end 47 of the hydraulic cylinder 44 that is designed to serve as a bearing surface to reduce wear of the metal piston rod 20 over time. Bushing 67 includes at least one circumferential recess for accommodating a seal, such as O-ring 69, which may help to capture any loose debris and helps to maintain a seal between the piston rod and the lock body and thereby seals the internal cavity.

In use, hydraulic rod system 20 utilizes pumping technology to drive the expansion of the rod. The pump may be mechanical, such as spring actuated, or osmotic, as will be described further below. In some embodiments, the pump is a separate independently formed element as shown in the illustrated embodiment of FIG. 1, and in other embodiments, the pumping is incorporated into the rod as a single piece, such that the rod is self-distracting, as will be described in additional examples below.

Figure 4:
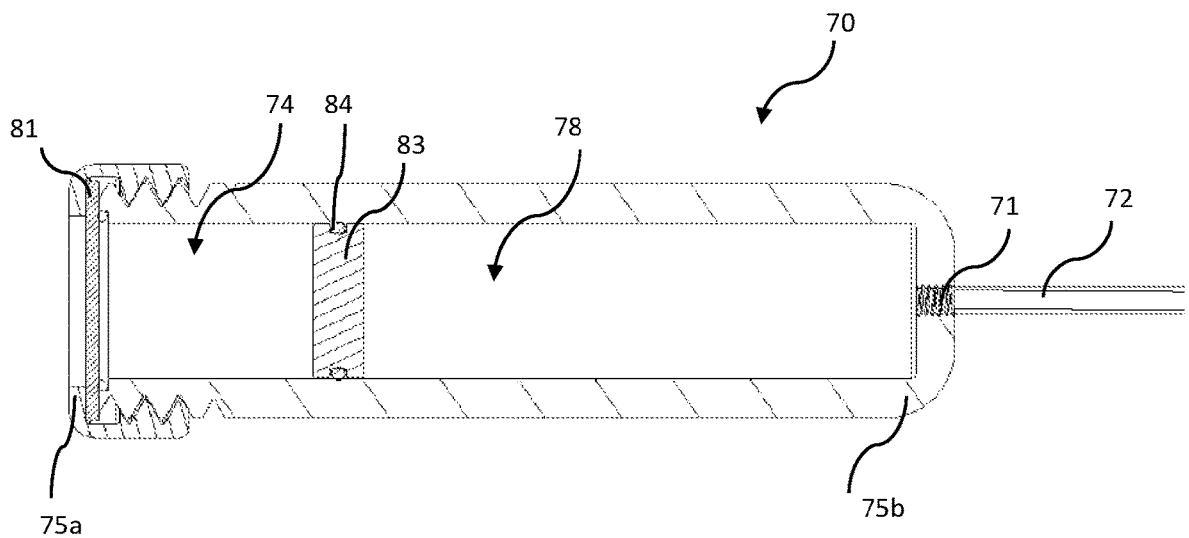
FIG. 4 is a cross-sectional view of the pump of the hydraulic rod system of FIG. 1.

FIGS. 1 and 4 show pump 70 of rod system 10 that is designed to be implanted sub-dermally in the patient for easier access for an operator after the initial surgery in the event a new pump with different pumping parameters is needed to be installed or a subsequent distraction is needed. The pump 70 is connected to the remainder of system 10 and is an osmotic pump that facilitates hydraulic expansion of the rods via axial translation of piston rod 20 in the internal cavity 46 of the hydraulic cylinder 44. After the initial distraction, pump 70 continues to work continuously to maintain spinal stabilization, maintain deformity correction, and prevent progression of the curving of the spinal column. Additionally, the continuously working pump 70 allows the rod to grow with the patient. The parameters of the pump are pre-determined such that the pump is designed to apply a constant target force on the piston rod 20 over time. However, the pump is designed so that the force applied to the rod by the pump is not high enough to over distract the spine.

The continuous nature of the osmotic pump prevents the periodic push and pull of the spine, which can occur with conventional and magnetic growing rod systems. As the patient grows, the continuously working pump allows the rod to grow with the patient at the same rate, resulting in minimal to no subsequent surgical intervention. Additionally, pump 70 has a structure and is formed of materials designed to prevent an increase in pressure inside the pump due to external mechanical loads exerted on the pump.

Referring to FIG. 4, pump 70 extends between an entrance first end 75a and an exit second end 75b and includes two chambers or zones—the first zone osmotic zone 74 contains an osmotic agent, such as salt NaCl, and the second zone hydraulic fluid zone 78 contains a hydraulic fluid, such as an incompressible, biocompatible fluid, e.g. sterile water or saline, blood, oils, and/or antibiotic infused fluid (to aid in infection prevention). Osmotic zone 74 is closer to first end 75a than is hydraulic zone 78, and accordingly hydraulic zone 78 is closer to second end 75b than the osmotic zone is to the second end. Osmotic zone 74 and hydraulic fluid zone 78 are separated by piston 83. Piston 83 has a round profile and includes a circumferential recess for receiving seal 84. In the illustrated embodiment, seal 84 is an O-ring for creating a seal between the piston and the side wall of the pump.

At first end 75a, pump 70 includes a semi-permeable membrane 81 separating the osmotic agent in the osmotic zone from the fluid in the patient's body. The semi-permeable membrane allows one component of a solution, such as water, to flow across the membrane while being impermeable to another component, such as the salt. The osmotic zone is designed to have a greater concentration of solutes, i.e. a higher salt concentration, so that fluid directionally moves into the osmotic zone from the patient's body. As the volume of fluid increases in the osmotic zone, pressure builds up and is applied to the piston 83, causing the piston to displace and translate in a direction toward second end 75b. As the piston 83 moves, pressure builds up on the hydraulic fluid in the hydraulic fluid zone 78, forcing the hydraulic fluid to exit the pump through coupling tube 72.

Near end 75b, pump 70 includes a coupling tube 72 that connects the pump to the hydraulic cylinder. In the illustrated embodiment, coupling tube is threadedly attached to the pump at attachment member 71 and couples to the rods at access port 48 of the hydraulic cylinder.

The pump 70 and the semi-permeable membrane 81 are designed such that the pumping rate is slightly faster than the maximum human pediatric growth. The rate of pumping is based on the cross-sectional area of the membrane 81, the thickness of the membrane, its water uptake properties, and the osmotic potential difference between the osmotic agent in osmotic zone 74 and outside the pump. The system is designed to achieve a constant pre-determined force applied on the piston rod.

In use, a surgeon first makes an incision in a patient's back, implants a plurality of pedicle screws or the like and implants one or more spinal rods 10 into the pedicle screws along the patient's spinal column. Static and piston rods 40, 20 are positioned within the tulip heads of the pedicle screws and affixed with a set screw or other fixing device. The rods are then initially distracted by injecting hydraulic fluid into access port 48 of the hydraulic cylinder, which initially corrects the spinal deformity. A syringe may be used to introduce the hydraulic fluid into the hydraulic cylinder to distract the rods. Due to the curvature of piston rod 20 and hydraulic cylinder 44, the rod system contours to the spinal curvature and allows for a longer expansion potential within the spinal column. Coupling tube 72 and pump 70 are attached to the rods and implanted sub-dermally.

After implantation, due to the differing salt concentrations in the patient's fluid outside of the pump 70 and inside the osmotic zone, water flows across the semi-permeable member 81 and into the osmotic zone 74. As the volume of water increases in the osmotic zone, pressure builds up on piston 83 and thus on hydraulic fluid zone 83 forcing the hydraulic fluid within the hydraulic fluid zone 78 through the coupling tube 72 and into access port 48. The fluid flows into hydraulic pressure chamber 50 and exerts a force on first end 22 of piston rod 20. Due to sleeve 52 surrounding the portion of piston rod 20 within internal cavity 46 of hydraulic cylinder 44, a sealed hydraulic pressure chamber is created. Thus, the force of the pump is translated to act on first end of piston rod 20. In the event a compressive force is applied to piston rod 20, lock assembly 56 engages with ball bearings 62 moving into ramped portions 58 to wedge the ball bearings in the ramp to lock the piston rod.

Figure 5:
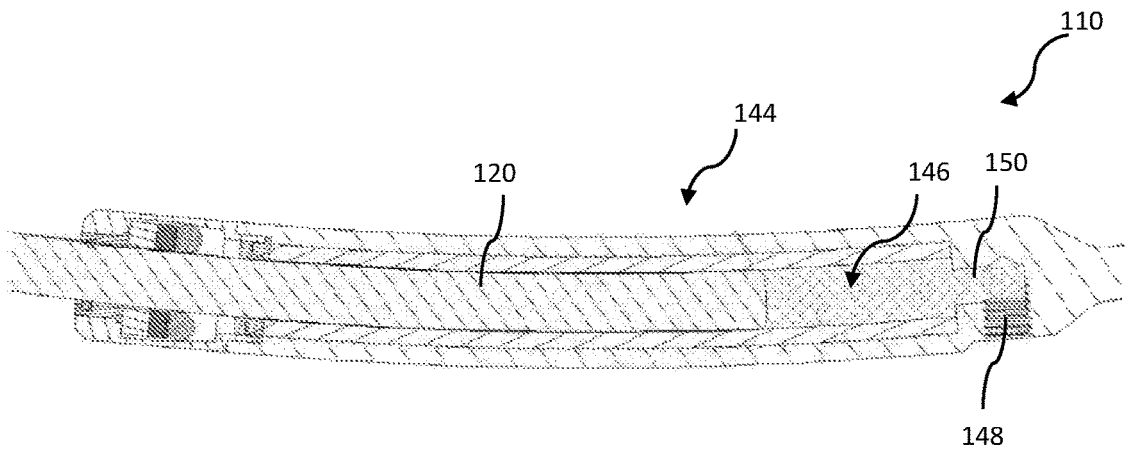
FIG. 5 is a cross-sectional view of an expandable hydraulic rod system according to another embodiment of the present disclosure.

In an alternate embodiment, shown in FIG. 5, a rod system 110 includes the pumping system integrated into the rods, and in particular the pumping system is integrated into the hydraulic cylinder 144. Like numerals refer to like elements in this embodiment, but with numbers in the 100 series. The major difference between rod systems 10, 110 is that an osmotic agent is held in the hydraulic pressure chamber 150 and a portion of the internal cavity 146. Access port 148 includes a semi-permeable membrane or plug that allows water from the patient which is external to the rods enter into the hydraulic cylinder. As the volume of water increases within the internal cavity 146, this volume exerts a force on piston rod 120 causing the piston to move in an expansion direction. In this example, the osmotic zone is formed within the internal cavity and drives the piston rod 120 directly without the need for a hydraulic fluid zone.

Figure 6:
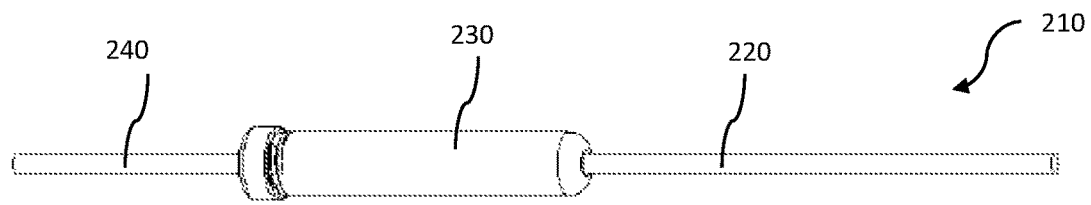
FIG. 6 is a perspective view of an expandable hydraulic rod system according to another embodiment of the present disclosure.
Figure 7:
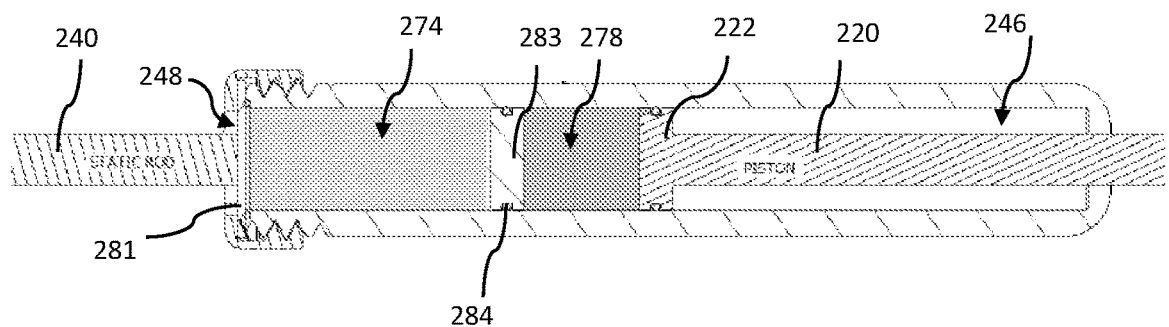
FIG. 7 is a cross-sectional view of the hydraulic rod system of FIG. 6.

FIGS. 6-7 show hydraulic rod system 210 similar to rod system 110, with like features not being discussed again here. System 210 includes a pumping system incorporated within the hydraulic cylinder such that the rod is a self-distracting rod, and in this example, hydraulic cylinder 244 includes two zones like pump 70 of rod system 10. In particular, hydraulic cylinder 244 includes osmotic zone 274 containing an osmotic agent and hydraulic fluid zone 278 containing hydraulic fluid. Osmotic zone 274 is positioned closer to static rod 240 than is hydraulic zone 278. Piston 283 separates the osmotic zone 274 and hydraulic zone 278 and includes a circumferential recess for receiving seal 284. In the illustrated embodiment, seal 284 is an O-ring. Hydraulic cylinder 244 also includes access port 248 in the form of a semi-permeable membrane that allows water to flow across the membrane and into the osmotic zone 274. End 222 of piston rod 220 includes a circumferential recess for receiving a seal, namely O-ring 284, to create a seal with the piston to allow pressure to build in the hydraulic cylinder. As the volume of fluid increases in the osmotic zone 274, pressure builds on piston 283 and consequently on the hydraulic fluid in zone 278. Due to seal 284, pressure is able to build in the hydraulic fluid zone which drives movement of piston rod 220 in an expansion direction.

Figure 8:
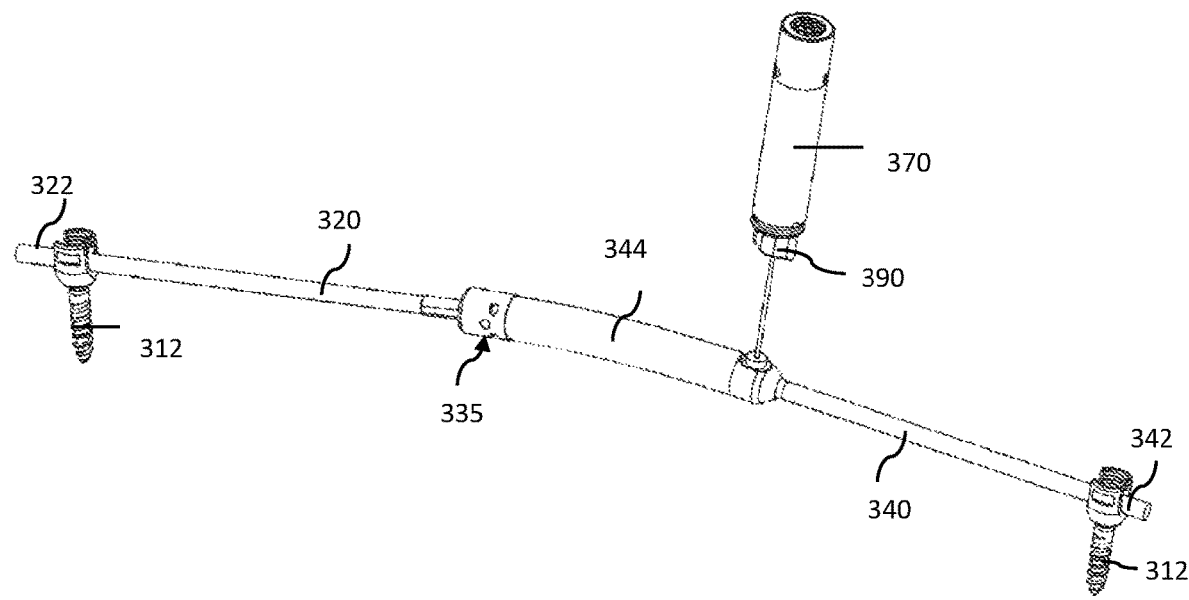
FIG. 8 is a perspective view of an expandable hydraulic rod system according to another embodiment of the present disclosure.

Referring to FIG. 8, hydraulic rod system 310 of the present disclosure is shown which is similar in many respects to rod system 110. Like numerals refer to like elements in this embodiment, but with numbers in the 300 series. Piston rod 320 and static rod 340 are each shown positioned within the tulip head of a respective pedicle screw 312. Static and piston rods 340, 320 are substantially similar to static and piston rods 40, 20 of rod system 10, the similar features of which will not be described again here. In this example, the hydraulic cylinder 344 and piston rod 320 are curved downward for fixation to the thoracic spine exhibiting a kyphotic curvature. Although in other examples the rod system may be curved in any desired manner, such as to accommodate lordotic curvature of the lumbar spine. Additionally, rod system 310 includes a lock body 351 having a lock assembly 356 identical to lock assembly 56 of rod system 10. Rod system 310 also includes a release feature 335 for disengaging the ball bearings 362 from the ramped portion 358 to allow the rods to contract, and in particular, to allow piston rod 320 to move in the contraction direction, opposite the direction of the arrow shown in FIG. 9A, as described in greater detail below. Additionally, hydraulic rod system utilizes osmotic pump 370 and quick connect member 390 for driving the hydraulic expansion of the rods.

Figure 9A:
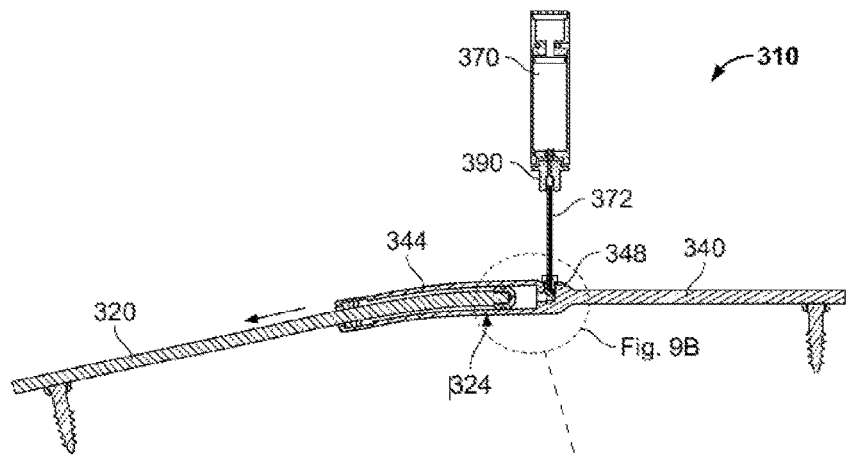
FIG. 9A is a cross-sectional view of the expandable hydraulic rod system of FIG. 8, and FIGS. 9B-9E are enlarged cross-sectional views focusing on the area of the hydraulic rod denoted by circle B of FIG. 9A depicting alternative piston rods of the hydraulic rod system of FIG. 8.
Figure 9B:
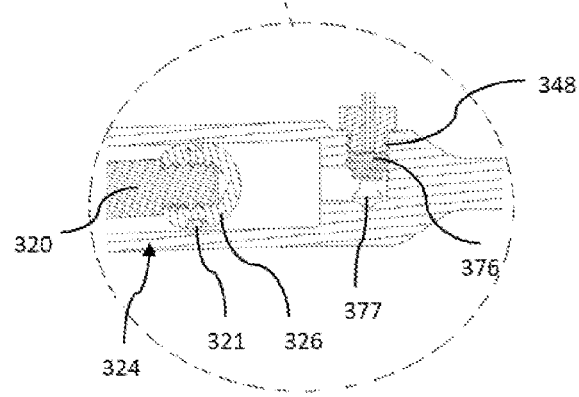

As shown in FIGS. 9A and 9B, piston rod 320 includes a rounded head 326 at end 324. Head 326 is designed to allow clearance of the curved hydraulic cylinder 344. Head 326 is attached to the end portion of piston rod, and in the illustrated embodiment, is threadedly attached thereto. Head 326 includes a circumferential recess for receiving seal 321, which is an O-ring in the illustrated embodiment. O-ring 321 maintains a seal between the piston rod 320 and the hydraulic cylinder 344 to create the hydraulic pressure chamber. Head 326 may be formed of a polymer, such as polyether ether ketone (PEEK).

Figure 9C:
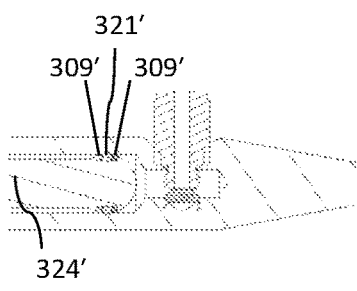
Figure 9D:
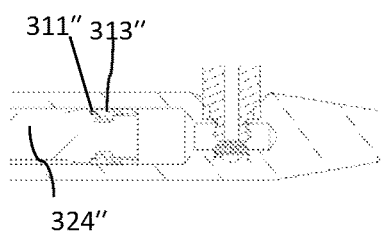
Figure 9E:
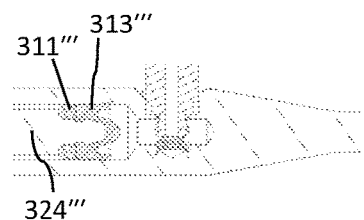

FIGS. 9C-9E show alternative configurations of head 326 of end portion 324 of the piston rod. FIG. 9C shows end 324' of the piston rod that includes head 326' which has a substantially rounded shape. Head 326' has a circumferential recess for receiving two bushings 309' and a seal or O-ring 321' between the bushings. Bushings 309' may be formed of a polymer such as PEEK and helps to energize the seal. Additionally, the polymer bushings prevent metal on metal contact of the piston with the hydraulic cylinder if a sleeve similar to sealing sleeve 52 of system 10 is not included within the internal cavity 346. FIGS. 9D and 9E show alternative variants of the piston rod and show cup seals 313", 313'" and adjacent rings 311", 311'" that support the cup seals and eliminate metal on metal contact of the piston rod with the hydraulic cylinder.

Figure 10A:
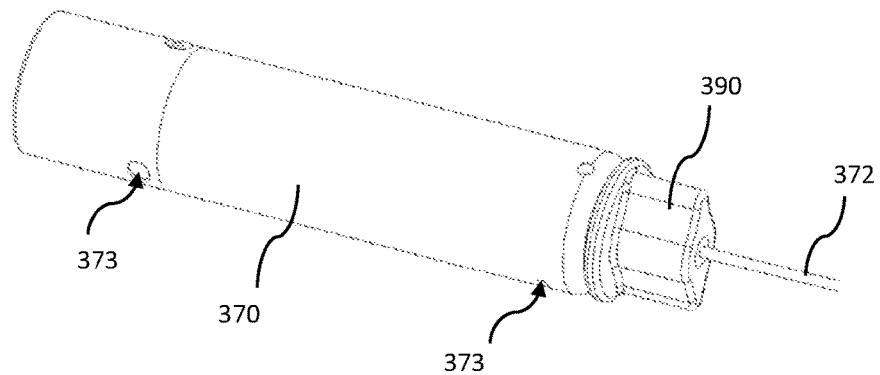
FIG. 10A is a perspective view of the assembled pump and quick connect feature of the rod system of FIG. 8, FIGS. 10B-10C are various side perspective views of the unassembled pump and quick connect feature of the rod system of FIG. 9.
Figure 10B:
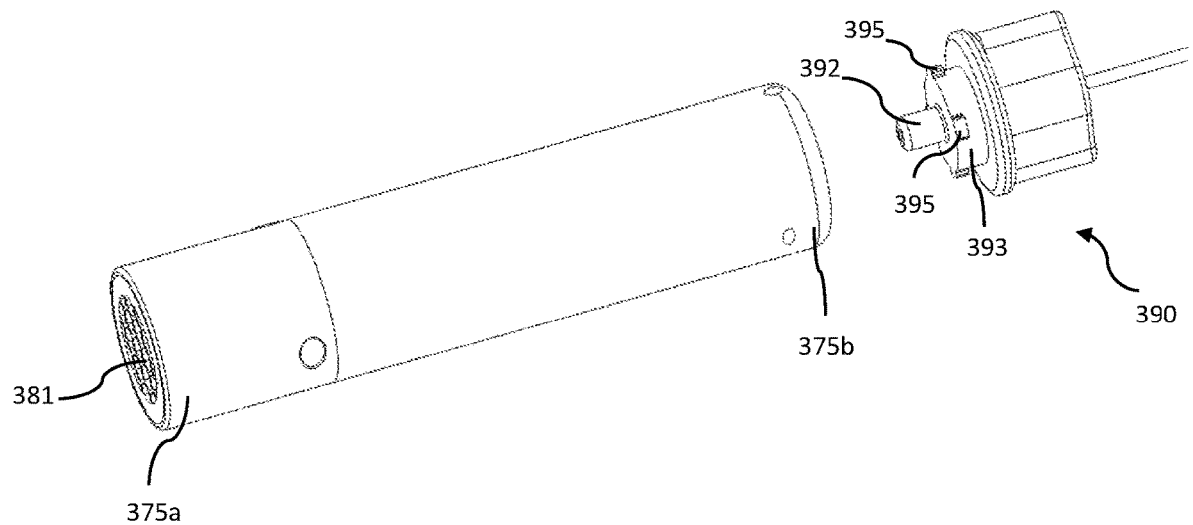
Figure 10C:
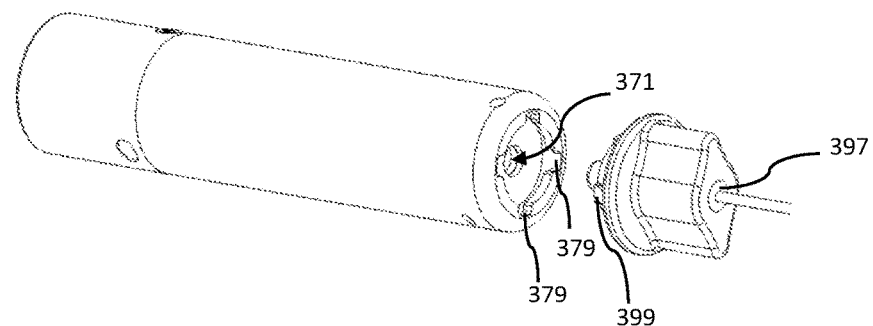
Figure 11A:
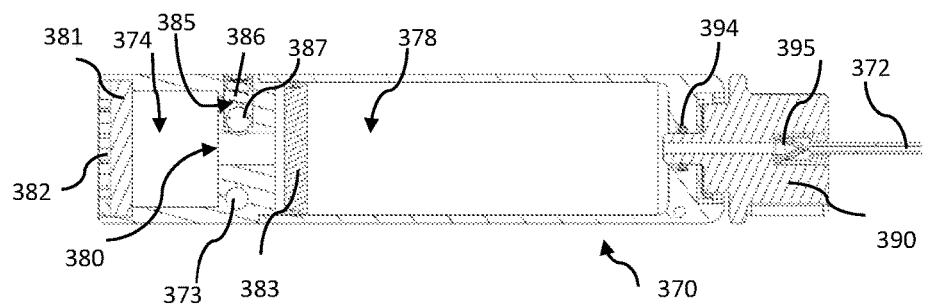
FIG. 11A is a cross sectional view of the assembled pump and quick connect feature of FIG. 10A.
Figure 11B:
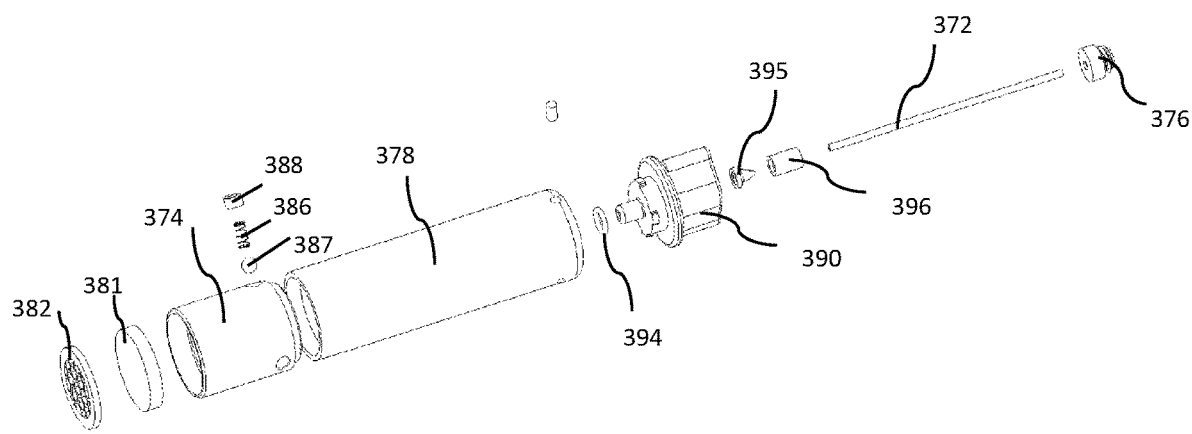
FIG. 11B is an exploded side view of the pump, quick connect feature, and coupling tube of the hydraulic rod system of FIG. 8.

FIGS. 10A-10C show various perspective views, and FIG. 11 shows a cross sectional view, of osmotic pump 370 and quick connect member 390 which attach to the hydraulic rods by coupling tube 372. Pump 370 extends from an entrance first end 375a to an exit second end 375b. Pump 370 includes semi-permeable membrane 381 at first end 375a which allows water to flow across the membrane and into osmotic zone 374. Osmotic pump 370 includes one or more, and in the illustrated embodiment, two suture holes 373 for receiving suture so that the pump can be securely fastened at the desired implant location of the pump.

Pump 370 includes two zones or chambers, osmotic chamber 374 and hydraulic fluid chamber 378 with the osmotic chamber positioned nearer to the first end 375a than the hydraulic fluid zone is to the first end. Osmotic chamber 374 is packed with an osmotic agent, such as salt, having a different concentration of solute, than the fluid of the patient's body and is connected to the hydraulic chamber 378, as shown in FIG. 12. In some cases, the osmotic chamber may also include an additional substance to eliminate air pockets. For example, the osmotic chamber may also include water, polyethylene glycol, or some other space filling fluid. Hydraulic chamber 378 contains a compressible hydraulic fluid. Support plate 382 is positioned adjacent the semi-permeable membrane 381 and includes at least one opening to allow fluid to flow through the membrane and into the osmotic chamber 374. For example, plate 382 may be formed of mesh. Support plate 382 provides structural support to resist deformation during pressuring of the pump system.

Pump 370 also includes a pressure relief system to allow for a constant pressure system. The pressure relief system includes hole 380 extending through a bottom portion of the osmotic chamber that allows the transfer of pressure from the osmotic chamber to the hydraulic chamber 378, and in particular allows a force to be exerted on piston 383 positioned within the hydraulic chamber and extending across the chamber. The pressure relief system further includes a spring-loaded ball that is disposed within channel 385 of the bottom portion of the osmotic chamber. Channel 385 extends through the outside surface of the osmotic chamber and intersects with hole 380. A central axis of channel 385 extends substantially perpendicular with a central axis of hole 380, although in other examples the central axis of the channel can extend at any non-zero degree angle to the axis of the hole. A portion of the channel has a width, measured in a direction from the first end 375a to second end 375b, that is larger than the diameter of ball 387. The width of channel 385 at the interface of the channel and hole 380 is smaller than the diameter of the ball such that a seating is defined at this interface. The diameter of the seating relative to the ball ensures that the ball seals the system and does not move into hole 380. During manufacture, the ball may be impacted when positioned within channel 385 to slightly deform the material at the seating to create a tight fit between the ball and the seating to create a seal. Bearing 388 is disposed within channel 385 adjacent the outer surface of the osmotic chamber and includes an opening through the bearing such that the bearing is annularly shaped. Spring 386 extends between bearing 388 and ball 387 to allow the ball the move from a sealed to a venting position.

After a pre-determined, target maximum pressure is reached, ball 387 is designed to no longer form a seal, such that pressure can continue to vent out of the system through channel 385. The pressure relief system allows for constant peak pressure to be applied to the rods. Because the pressure is able to be vented out of the system, the pressure does not disadvantageously ramp up when the piston rod 320 has reached its maximum expansion amount.

Pump 370 includes an attachment feature at second end 375b to connect the pump to quick connect member 390. As shown in FIG. 10C, pump 370 includes hole 371 extending into hydraulic fluid chamber 378 for fluid to flow from the pump to the quick connect member to tube 372 and then to hydraulic cylinder 344. Hole 371 includes a circumferential recess for receiving a seal 394, such as an O-ring. Pump 370 also includes spaced apart recesses 379 to matingly engage with tabs 399 of the quick connect member 390 to secure the quick connect member to the pump.

Rod system 310 also includes quick connect member 390 that is designed to attach to pump 370 at second end 375b of the pump and also connect to coupling tube 372. Quick connect member 390 includes projection 392 which is sized and shaped to fit within hole 371 of the pump. Projection 392 has an opening extending through the body of the quick connect member to allow fluid to flow through the body and into coupling tube 372. Quick connect member 390 also includes a plurality of spaced apart tabs 399 sized and shaped to fit within recesses 379 of pump 370. Although, other attachment features known in the art can be used to attach the quick connect member to the pump. Quick connect member 390 also includes a one-way pressure valve 395 designed to prevent any back pressure from entering the hydraulic growing rod.

The opening extending through the body of the quick connect member 390 leads into coupling tube 372 which includes a threaded coupler 376 for connecting to threaded access port 348 of the hydraulic cylinder 344. Coupler 376 has an opening extending through it to allow fluid to enter into the rods.

Figure 12A:
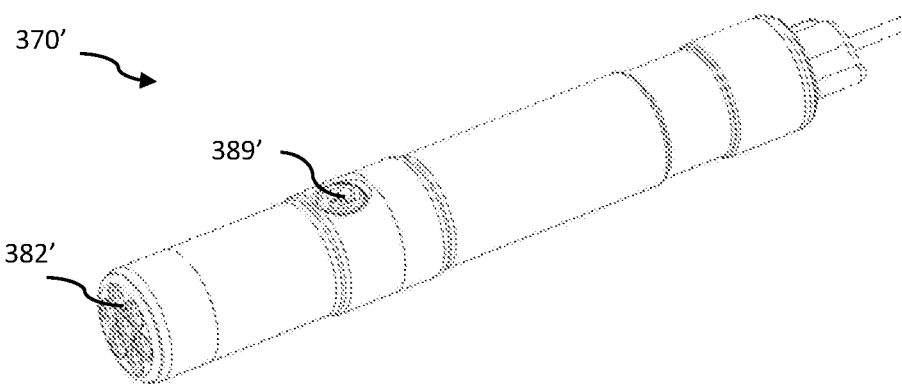
FIGS. 12A-12C are a perspective side view, cross-sectional view, and exploded view of an assembled pump according to another embodiment of the present disclosure.
Figure 12B:
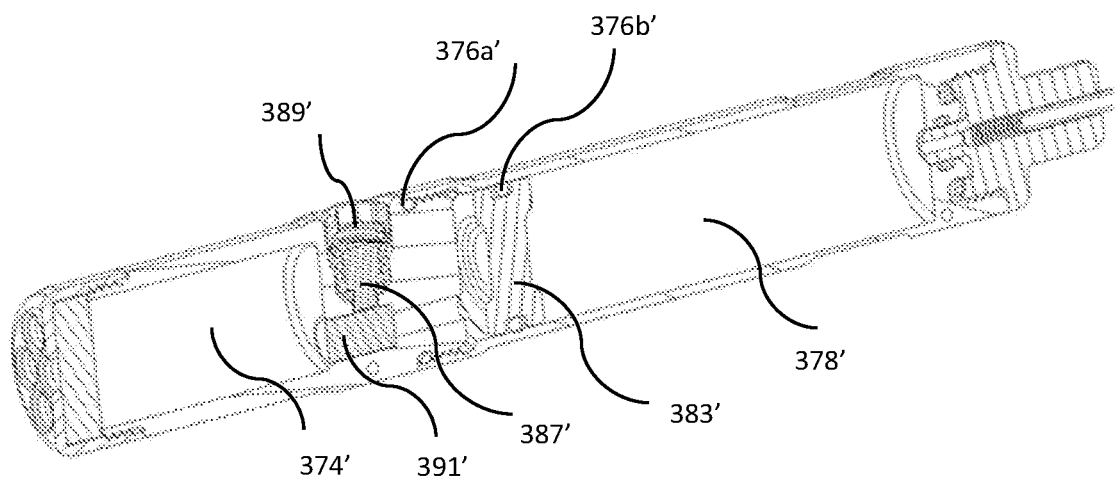
Figure 12C:
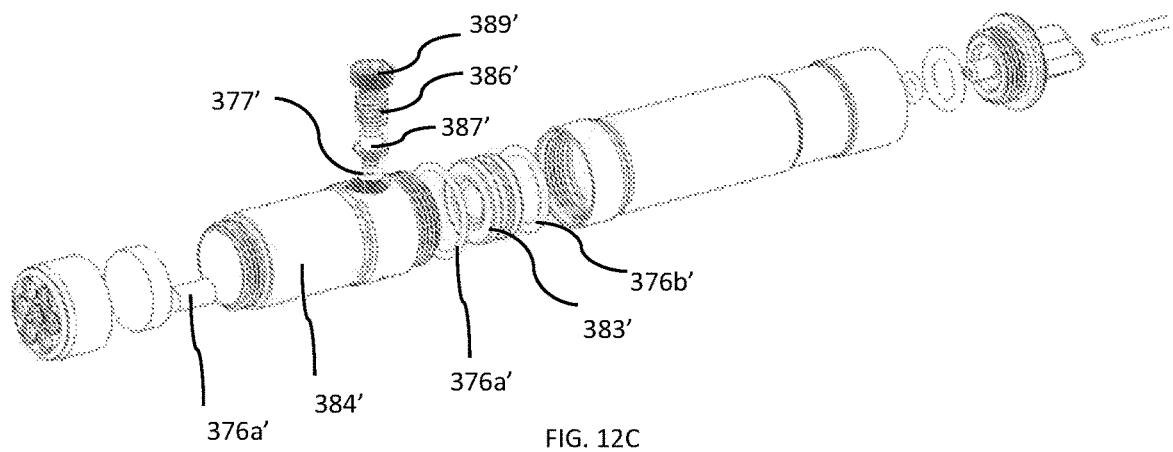

FIGS. 12A-12C show an alternative embodiment of a pump 370' that functions in the same manner as pump 370, the structural differences of which are noted herein. As best shown in FIG. 12A, support plate 382' has larger openings for allowing the fluid to pass through the support plate and into the pump. Further, the pressure relief system includes O-ring 377' sealingly surrounding spring-loaded plug 387' which is configured to bear on porous plug 391' positioned within channel 380'. Set screw 389' secures the pressure relief system within the osmotic zone. As shown in FIGS. 12B and 12C, O-rings 376a' and 376b' sealingly engage osmotic zone 374' and piston 383' respectively Like pump 370, pump 370' is configured to attach to quick connect member 390 in much the same manner.

Figure 13A:
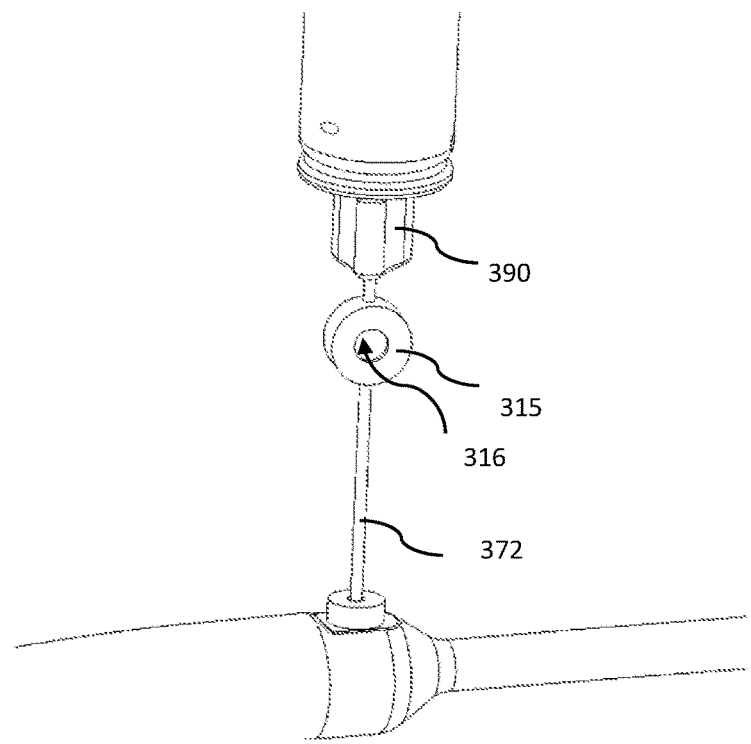
FIG. 13A is a perspective view of an injection port used in conjunction with the pump, quick connect feature, and coupling tube of FIG. 11 in accordance with an embodiment of the present disclosure.
Figure 13B:
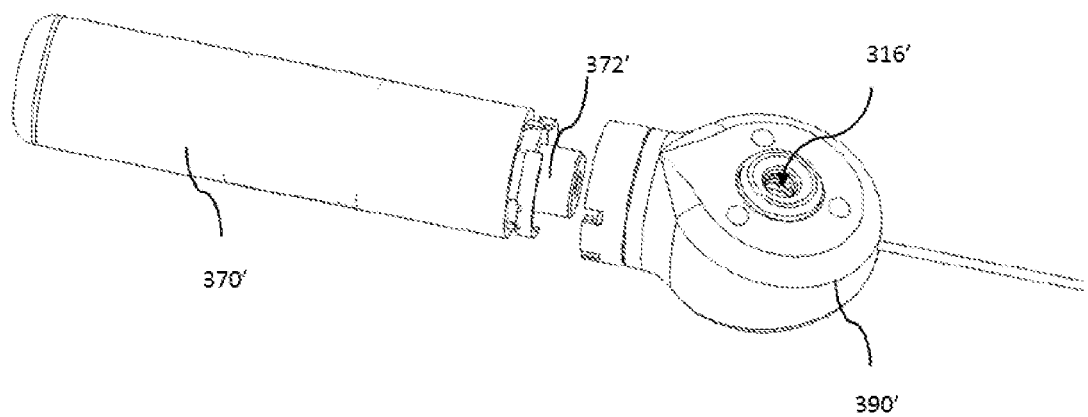
FIG. 13B is a perspective view of an alternative injection pump in accordance with another embodiment of the present disclosure.
Figure 14:
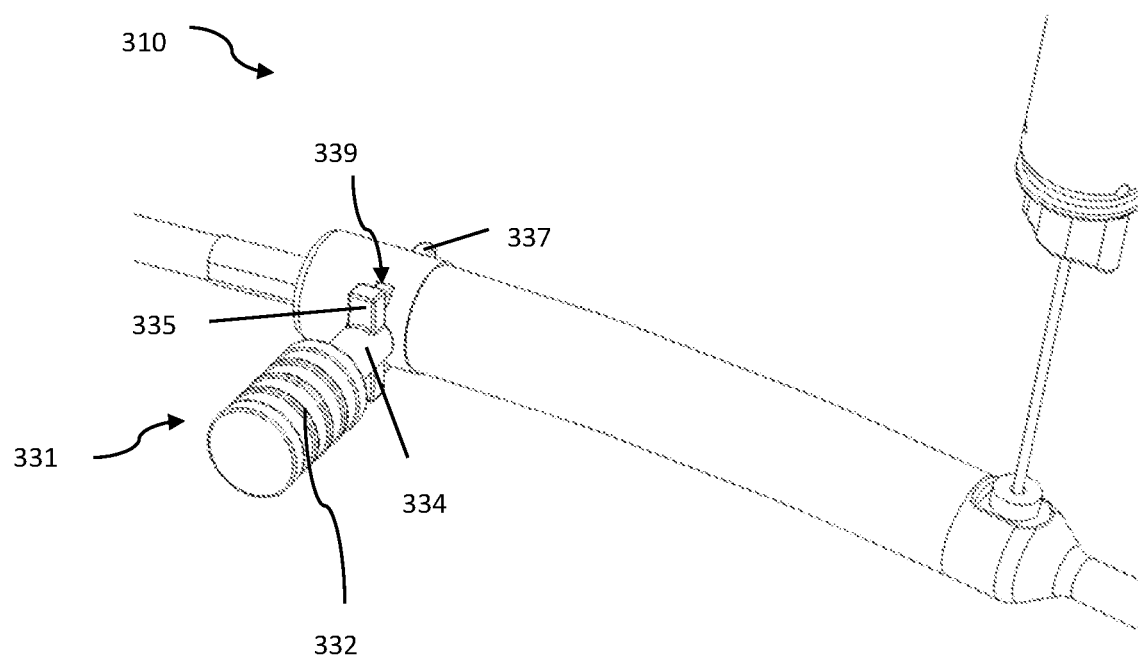
FIG. 14 is a perspective view of a release instrument in conjunction with the hydraulic rod system of FIG. 8.

FIG. 13A shows coupling tube 372 which includes injection port 315 disposed between the quick connect member 390 and the threaded coupler 376. Injection port 315 includes opening 316 for injecting fluid into the system for distraction of the spine. A syringe may be used to inject the fluid into the injection portion. In alternative examples, the injection port 315 may include features that enable a surgeon to more easily locate the injection port within the body percutaneously. Alternatively, as shown in FIG. 14, the injection port can be formed in the quick connect member 390'. As shown in this example, the pump 370' includes a projection 372' for engagement with a corresponding recess in quick connect member 390'. A surgeon or operator can inject fluid into opening 316' of the quick connect member 390' to distract the spinal rods.

The piston rod 320 may also include a strain gage or other force measurement to monitor in-vitro forces on the spinal rod. A strain gage may also be included on pump 370 to measure the pressure of the pump.

In use, rod system 310 is implanted in a spinal column in a substantially similar manner as rod system 10. A surgeon implants one or more spinal rods including static rod 340 and piston rod 320 on the patient's spinal column via attachment of the rods with pedicle screws. Typically, the construct is bilateral with two rod systems 310 implanted. After the rods are secured to the pedicle screws the coupling tube 372 is attached to the rods at access port 348, and the coupling tube 372 is run from the spinal construct through the muscle so that pump 370 is positioned closer to the surface of the patient. Suture is positioned through the suture holes of the pump to securely fasten the pump at the desired location. The rods are initially distracted by injecting fluid into the system either at access port 348 or injection port 315 via a syringe. The fluid flows into hydraulic pressure chamber 350 and due to the sealed system a hydraulic pressure chamber is created in the hydraulic cylinder 344. The force builds on end 322 of piston rod 320 forcing the rod to move in the expansion direction thereby expanding the length of the rods. This initial distraction of the rods is performed to correct the spinal deformity, and the continuously working pump 370 holds the corrected position of the spine and allows the rod to grow with the patient's growth.

After initial distraction, osmotic pump 370 continuously works to allow the rods to grow without requiring later distractions. Although, is a strain gage is employed with the system, the surgeon can identify if rod adjustment is needed. For example, if the force on the piston rod 320 is lower than expected, the surgeon can subsequently perform a one-time distraction. This information may be transmitted by Bluetooth® or other known transmission methods.

If after initial distraction, compression is applied to piston rod 320, the one-way lock assembly 356 prevents piston rod 320 from collapsing or moving in the retraction direction as ball bearing 362 becomes wedged into ramped portion 358 causing the ball to bear on piston rod 320 to lock the rod in place. Rod 320 includes a release mechanism 335 for disengaging the lock assembly 356 to allow the piston rod 320 to move in a contraction direction, opposite the expansion direction.

Figure 15:
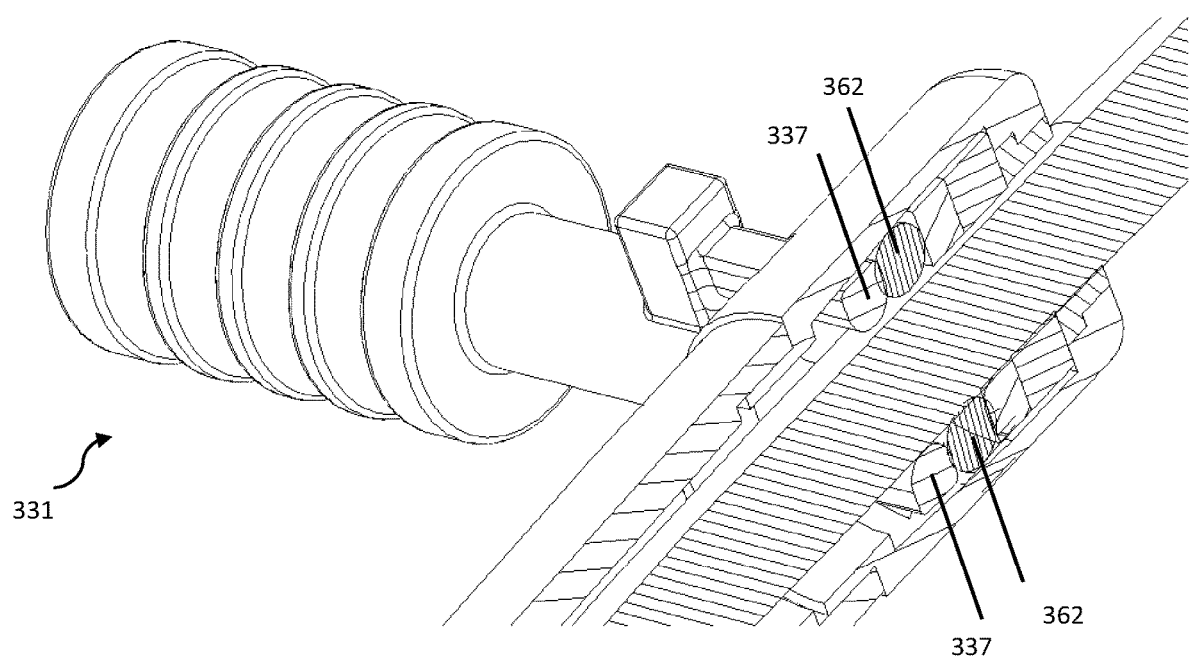
FIG. 15 is a cross-sectional view of the release instrument of FIG. 14 in conjunction with the rod system of FIG. 8.

As shown in FIGS. 14-15, in the event that the piston rod 320 is expanded too far and it is desired to contract the piston rod, lock body 351 includes at least one access hole extending through both sides of the lock body. In the illustrated embodiment, release mechanism 335 includes a plurality of spaced apart holes sized and shaped to receive a release instrument 331 which is designed to move the two ball bearings 362 away from the ramped portion 358, as shown in FIGS. 14-15. Two access holes 339 of the release mechanism 335 are aligned with the ramped portions 358 of the lock body 351.

Release instrument 331 includes handle 332 with shaft 334 extending distally from the handle. Two opposing lateral members 335 extend outwardly from shaft 334. Forked ends or prongs 337 extend distally from lateral members 335 to form the forked shape of the instrument and are shaped to fit into the ramped portions 358.

In use, forked ends 337 are positioned within the access holes of the release mechanism 335 as shown in FIG. 15 such that the forked ends 337 are positioned within the ramped portion 358 to bias or dislodge the ball bearings from the ramped portion to allow the piston rod to move freely in either the contraction or expansion direction. The forked ends 337 are maintained in the position shown in FIG. 15 while the piston rod is moved in the contraction direction to shorten the length of the rods as needed.

In an alternative embodiment, the rod system may include a one-way locking mechanism that utilizes one or more cam or wedge members instead of or in combination with ball bearings 62, 362 of rod systems 10, 310.

Figure 16:
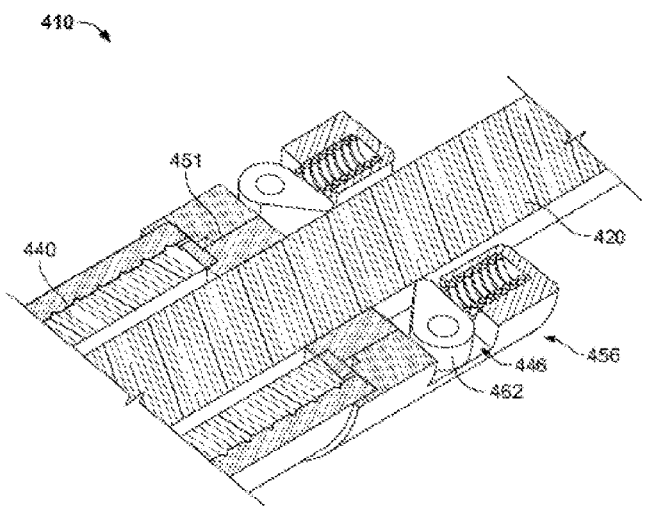
FIG. 16 is a cross-sectional view of an alternative hydraulic rod system depicting an alternative locking mechanism according to another embodiment of the present disclosure.

FIG. 16 shows rod system 410 that includes lock body 451 connected to static rod 440. The lock body may be integral with the static rod or it may be two pieces welded or otherwise securely fixed together. Lock body 451 includes lock assembly 456 which engages piston rod 420 to prevent the piston rod from moving in the contraction direction while allowing the rod to move in the expansion direction. Lock assembly 456 includes cam 462 disposed within cavity 446 of lock body 451. As a contraction force is applied to the piston rod 420, the cam 462 engages the rod to lock the rod thereby preventing it from moving in the contraction direction.

Figure 17:
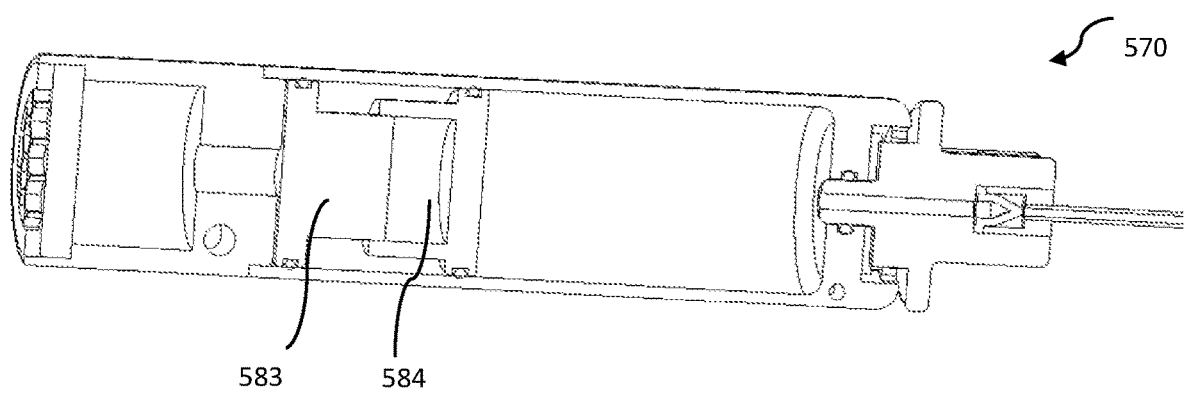
FIG. 17 is a cross-sectional view of an alternative pump for use with the hydraulic rod system of FIG. 8.

FIG. 17 shows an alternative osmotic pump 570 for expansion of the rods according to another embodiment of the present disclosure. Pump 570 is similar to pump 370, the similar features of which will not be described at length again here. Pump 570 includes an osmotic chamber and a hydraulic fluid chamber with two telescoping pistons 583, 584 in between. The pump is designed so that when the target pressure value is achieved, the telescoping pistons move together. As the pistons move toward one another, the pressure in the system reduces.

Alternatively, to achieve a pressure relief system, a pump, like pumps 370 or 570, may include burst zones incorporated on the piston. In this manner, at least one section of the pump may include a relatively thinner wall section as compared to the rest of the pump. The thinner wall section is designed to yield or deform which allows for an increase of volume in the pump thereby reducing the pressure. In yet another embodiment, the pump may include at least one deformable crumple zone in the pump. As pressure increases within the pump, the crumple zone expands in an accordion fashion causing the volume of the zones to increase thereby reducing the pressure. In both examples, the amount of expansion and/or deformation is controlled such that the amount of pressure remains controlled.

Figure 18:
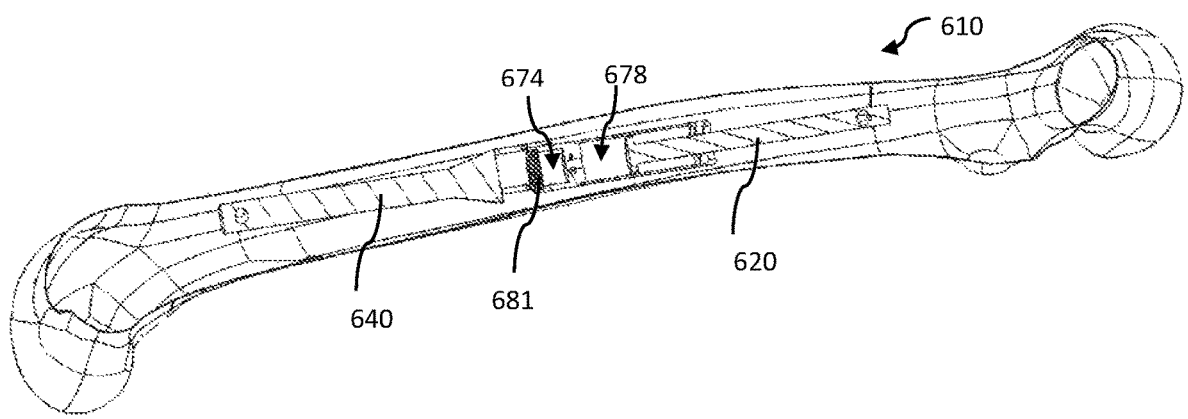
FIG. 18 is a cross-sectional view of hydraulic rod system according to yet another embodiment of the present disclosure shown implanted in a long bone.

In yet another embodiment of the present disclosure, FIG. 18 shows rod system 610 that includes a self-distracting intramedullary nail or static rod 640 and piston rod 620 that form an expandable rod system for implantation within a long bone for correction of a deformity and/or stabilization of a bone while allowing lengthening of the bone during growth. The static rod is attached to the bone via a fixation member such as a traditional bone screw, and the piston rod is attached by a fixation member that allows expansion of the piston rod.

The rod system includes a pumping system within the rods such that a separate pumping element, like pump 370 is not required to be implanted. For example, static rod 640 includes semi-permeable member 681 that leads into osmotic chamber 674 that allows water to flow into the chamber to pressurize piston rod 620 for movement of the piston rod in the expansion direction. Accordingly, the piston rod expand as a direct result of the bodily fluid entering the osmotic chamber, as this allows for a more efficient expansion of the rod.

Static rod 640 may optionally include a hydraulic fluid chamber 678 and a piston so that as the volume of fluid builds up in the osmotic chamber, the piston translates into the hydraulic fluid chamber causing hydraulic fluid to force the piston rod to expand. The pump is designed to allow for a controlled expansion of the piston rod over time to allow the rod to grow as the patient grows.

Figure 19:
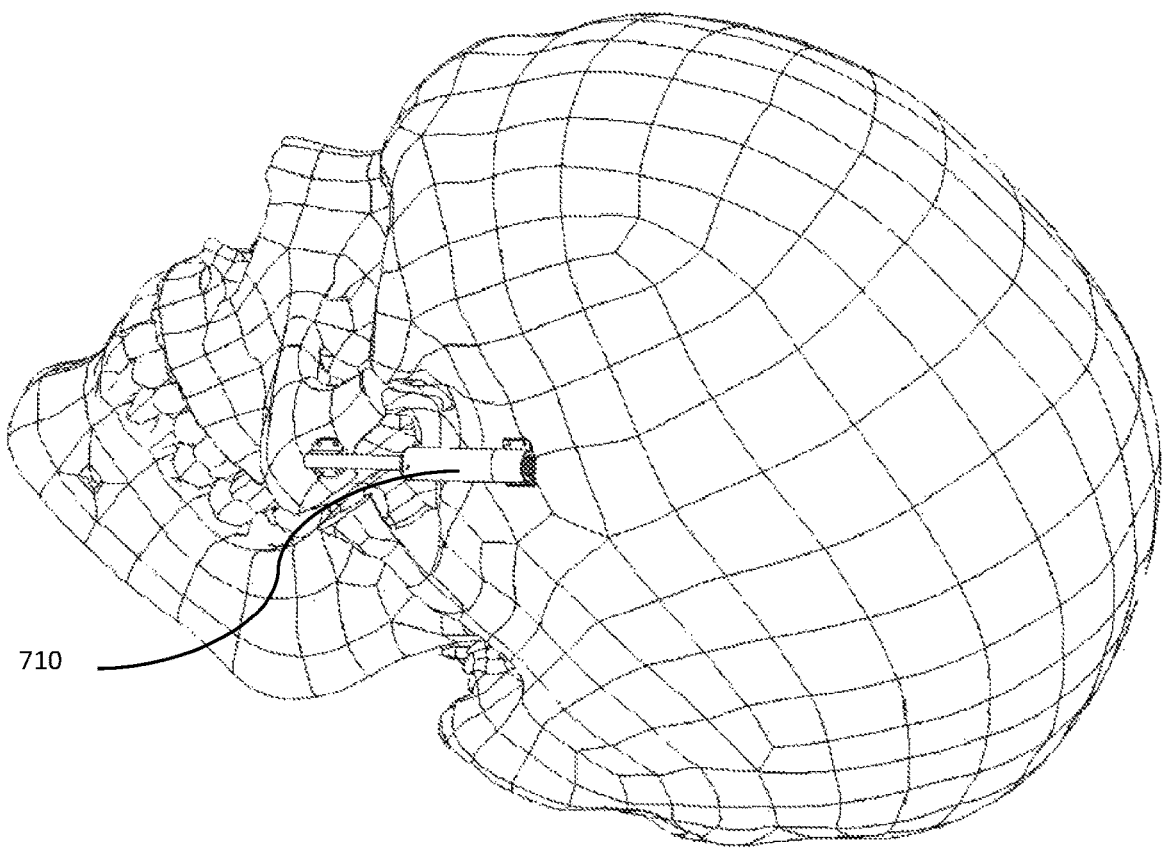
FIG. 19 is a perspective view of a hydraulic rod system according to another embodiment of the present disclosure shown implanted in a skull.
Figure 20:
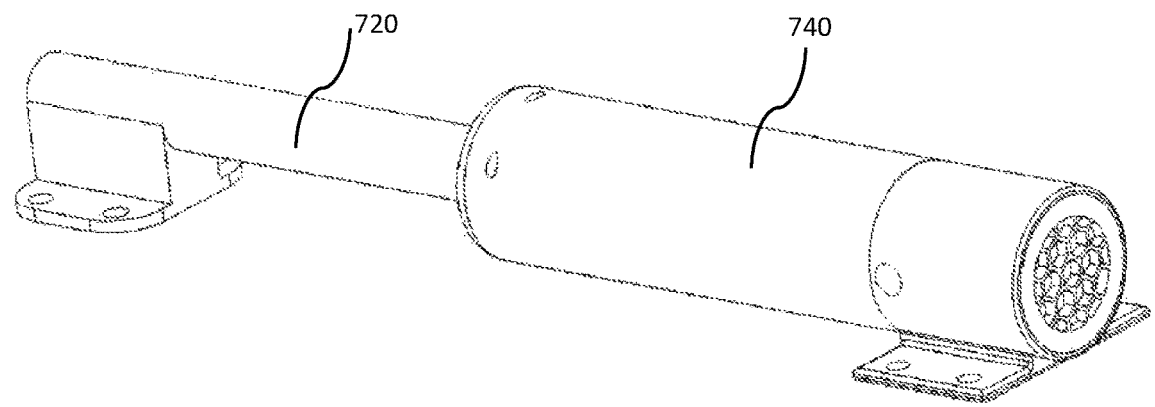
FIGS. 20-21 are perspective and cross-sectional views, respectively, of the rod system of FIG. 19.
Figure 21:
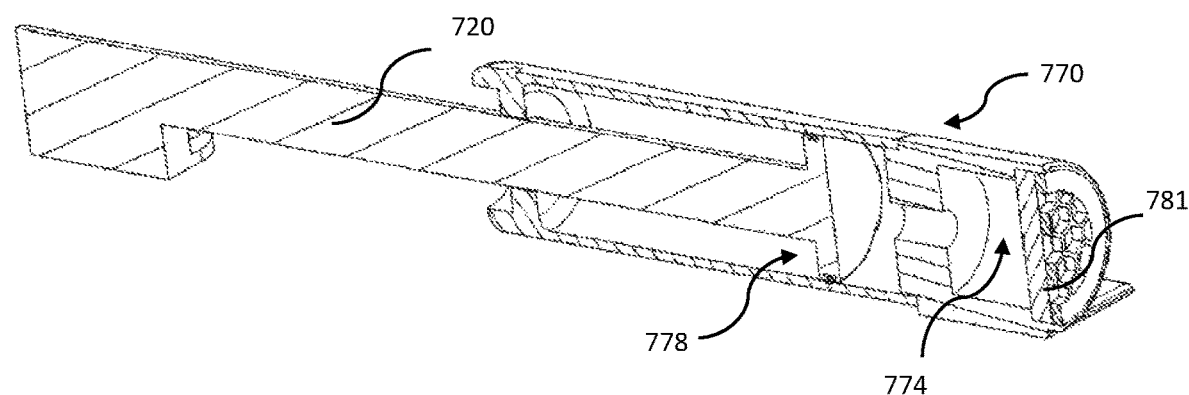

In yet another embodiment of the present disclosure, FIGS. 19-21 show rod system 710 which includes a self-distracting rod for midface implantation and distraction. For example, rod system 710 may be advantageously used for treating midfacial retrusion. Rod system 710 includes a static rod portion 740 and a piston rod portion 720 which are secured to the bone by fixation members or plates 712. Static rod portion 740 includes pump system 770 for transmitting pressure on piston rod 720 to distract the rod. Static rod portion 740 includes semi-permeable membrane 781 that allows water to access osmotic chamber 774 packed with an osmotic agent. Static rod 740 may optionally include hydraulic chamber 778 in which piston rod 720 is moveably positioned, although preferably, the fluid entering the osmotic chamber directly acts on the piston rod causing it to move in the expansion direction, as described above with reference to rod system 610. As fluid, such as water, from the patient's body flows through the semi-permeable membrane 781 at a predetermined rate, as discussed above with reference to pump 70, the piston rod 720 moves outward at a constant rate. Once the desired distraction is achieved, the osmotic agent may be aspirated or diluted to eliminate the osmotic potential. Alternatively, the static rod may include an internal stop to prevent the piston rod from expanding beyond that point.

After distraction, rod system 710 may be surgically removed. Alternatively, the device may remain implanted. A portion or the entirety of entire device may be formed of resorbable materials, such as polylactic acid (PLA), such that the device can be slowly broken down by the body.

Figure 22:
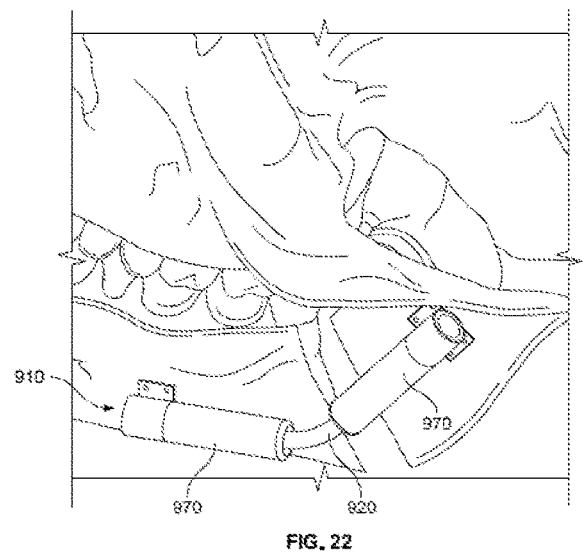
FIG. 22 is a perspective view of a hydraulic rod system according to another embodiment of the present disclosure shown implanted in a mandible.

Rod system 710 may be employed in procedures for correcting Robin sequence. Accordingly, the rod system may be sized and shaped for mandibular distraction, Additionally, for mandibular distraction, it may be desirable to lengthen the mandibular in two directions, anteriorly and caudally. In such an instance, a dual pump configuration may be utilized, as shown in FIG. 22. Rod system 910 shows a dual-pump rod system configuration which utilizes two pumps 970 with a curved piston rod 920 situated between them.

Figure 23:
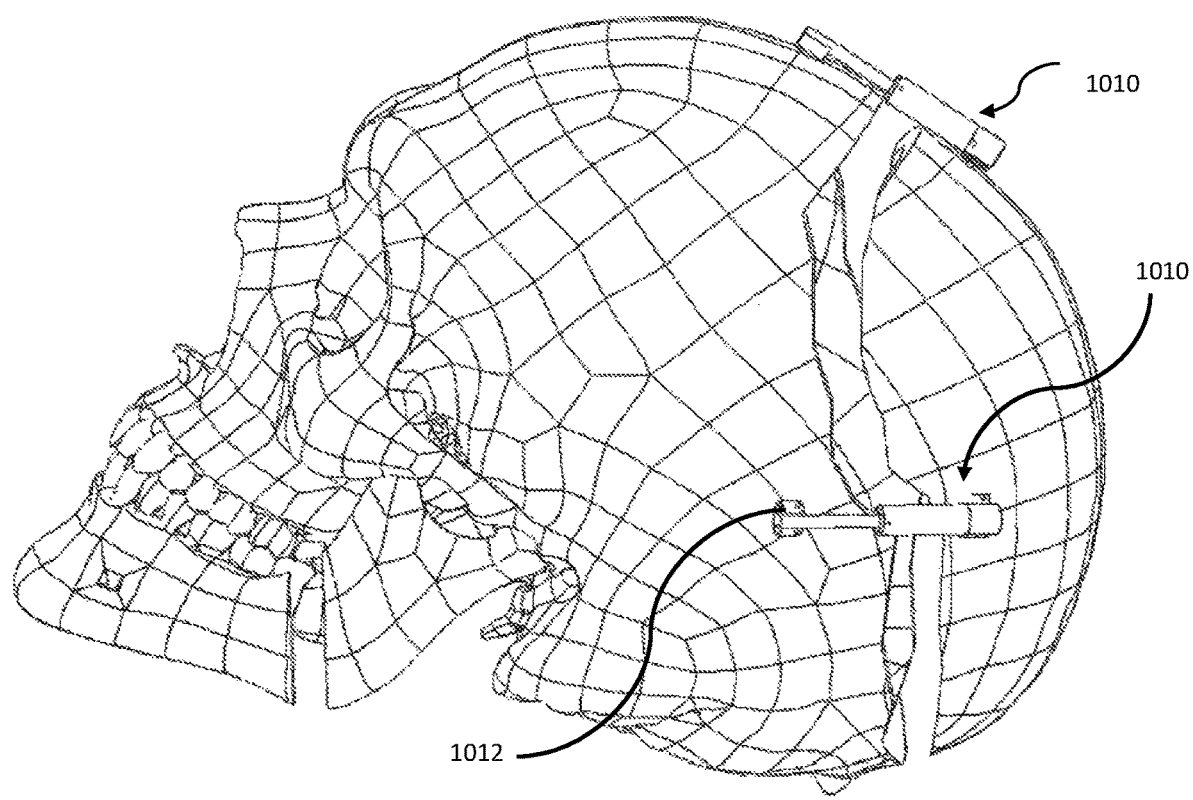
FIG. 23 is a perspective view of the hydraulic rod system of FIG. 19 according to yet another embodiment of the present disclosure shown implanted in a skull.

A device similar to rod system 710 may also be utilized in craniosynotosis as shown in FIG. 23. In this embodiment, at least one rod system 1010 is affixed to the skull on opposing sides of the cranial sutures. However, in this example, the rod systems would desirably be secured by resorbable plates 1012, so that new bone does not form around the metal plates.

It will be appreciated that the features described in connection with individual embodiments may be shared with others of the described embodiments. For example, rod systems 610, 710, 910, and 1010 may employ a one-way lock assembly similar to lock assemblies 56, 356 of rod systems 10, 310. Additionally, the systems including system 10 may include a release mechanism and release instrument similar to those described in connection with system 310.

Additionally, the present disclosure may also include various kits based on the devices discussed above. For example, kits of the present disclosure may include at least one rod including a piston rod and a static rod, and instructions for inserting a desired amount of osmotic agent within the pumping system to achieve a desired pump rate and expansion amount. The kit may include self-distracting rods with the osmotic zone integrated into the a portion of the rod or the kit may include a separate pump. The kit may include a quick connect feature and a coupling tube. The kit may include a release instrument 331 for unlocking the rod systems to allow the piston rod to move in the contraction direction. The kit may be included in a single package or in separate packages which are later brought together as a kit.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An expandable rod system comprising:
a first rod portion having an internal cavity;
a second rod portion sealingly positioned within the internal cavity of the first rod portion, and moveable in a first axial direction relative to the first rod portion;
an osmotic chamber for receiving an osmotic agent to facilitate movement of the second rod portion to expand the rod system;
a lock assembly engageable with the second rod portion to prevent the second rod portion from moving in a second axial direction, the lock assembly including a tapered ramped portion and a bearing member, the bearing member moveable within the tapered ramped portion such that when compression forces are imparted on the second rod portion, the bearing member is wedged in the tapered ramped portion; and
an access hole to permit access of an instrument through the access hole such that when the bearing member is wedged in the tapered ramped portion, the instrument may dislodge the bearing member from the tapered ramped portion.

2. The rod system of claim 1, comprising a pressure relief system configured to relieve fluid pressure from the osmotic chamber by venting fluid out of the rod system from within the osmotic chamber, the pressure relief system comprising a channel and a spring-loaded ball disposed in the channel and biased to selectively close or open the channel in response to pressure across the channel, wherein the channel extends between a hole that is in fluid communication with the osmotic chamber and an external surface of the osmotic chamber.

3. The rod system of claim 2, further comprising a hydraulic chamber between the osmotic chamber and the second rod portion and wherein the hole allows the transfer of pressure from the osmotic chamber to the hydraulic chamber.

4. The rod system of claim 1, further comprising a semi-permeable membrane fluidly connected to the osmotic chamber for allowing fluid from the patient to flow across the membrane and into the osmotic chamber.

5. The rod system of claim 1, wherein when compression forces are imparted on the second rod portion, the bearing member is wedged in the tapered ramped portion.

6. The rod system of claim 1, wherein the instrument is configured to dislodge the bearing member and push the bearing member up the ramped portion to allow movement of the second rod portion relative to the first rod portion in the second direction.

7. The rod system of claim 1, wherein the bearing member is a ball.

8. The rod system of claim 1, wherein the second rod portion and the internal cavity are curved.

9. The rod system of claim 1, further comprising a pump configured for implantation sub-dermally in a patient, the pump including the osmotic chamber and being fluidly connected with the internal cavity of the first rod portion.

10. The rod system of claim 9, wherein the pump includes a hydraulic fluid chamber for receiving hydraulic fluid.

11. The rod system of claim 9, further comprising a one-way pressure valve to prevent pressure from traveling from the internal cavity to the pump.

12. The rod system of claim 1, wherein the second rod portion is continuously moveable relative to the first rod portion.

13. The rod system of claim 12, wherein the second rod portion is moveable at a constant rate.

14. The rod system of claim 1, wherein the rod system is configured for implantation on a patient's spinal column.

15. The rod system of claim 1, wherein the first rod portion is adapted for connection with a first bone and the second rod portion is adapted for connection with a second bone.

16. An expandable rod system comprising:
a first rod portion having an internal cavity;
a second rod portion sealingly positioned within the internal cavity of the first rod portion, and moveable in a first axial direction relative to the first rod portion;
an osmotic chamber for receiving an osmotic agent to facilitate movement of the second rod portion to expand the rod system;
a semi-permeable membrane fluidly connected to the osmotic chamber for allowing water flow across the semi-permeable membrane and into the osmotic chamber;
a lock assembly engageable with the second rod portion to prevent the second rod portion from moving in a second axial direction, the lock assembly including a tapered ramped portion and a bearing member, when the rod system is in a locked configuration, the bearing member is wedged in the tapered ramped portion and bears on the second rod portion to lock the second rod portion relative to the first rod portion; and
an access hole to permit access of an instrument through the access hole such that when the bearing member is wedged in the tapered ramped portion, the instrument may dislodge the bearing member from the tapered ramped portion.

17. The rod system of claim 16,
a pressure relief system configured to relieve fluid pressure from the osmotic chamber by venting fluid out of the rod system from within the osmotic chamber, the pressure relief system comprising a channel and a spring-loaded plug biased to selectively close or open fluid communication between the channel and an exterior of the osmotic chamber in response to pressure in the channel.

18. The rod system of claim 17, comprising a porous plug located in the channel.

19. The rod system of claim 16, wherein the instrument is configured to dislodge the bearing member and push the bearing member up the ramped portion to allow movement of the second rod portion relative to the first rod portion in the second direction.

* * * * *